United States Patent
Persyn et al.

(10) Patent No.: US 7,758,778 B2
(45) Date of Patent: *Jul. 20, 2010

(54) METHODS FOR PREPARING BIODEGRADABLE MICROPARTICLE FORMULATIONS CONTAINING PHARMACEUTICALLY ACTIVE AGENTS

(75) Inventors: Joseph T. Persyn, Lakehills, TX (US); Joseph A. McDonough, Helotes, TX (US); Neal K. Vail, San Antonio, TX (US); Darren E. Barlow, Floresville, TX (US); Albert M. Zwiener, San Antonio, TX (US); Eliot M. Slovin, Arlington, TX (US)

(73) Assignee: Southwest Research Institute, San Antonio, TX (US)

( * ) Notice: Subject to any disclaimer, the term of this patent is extended or adjusted under 35 U.S.C. 154(b) by 843 days.

This patent is subject to a terminal disclaimer.

(21) Appl. No.: 11/220,430

(22) Filed: Sep. 7, 2005

(65) Prior Publication Data

US 2007/0053989 A1  Mar. 8, 2007

(51) Int. Cl.
*B29B 9/00* (2006.01)
*A61J 3/00* (2006.01)

(52) U.S. Cl. ............... 264/8; 264/5; 264/7; 264/15; 425/6; 425/8; 424/425; 424/463; 424/484

(58) Field of Classification Search ............... None
See application file for complete search history.

(56) References Cited

U.S. PATENT DOCUMENTS

| | | | |
|---|---|---|---|
| 3,015,128 A | 1/1962 | Somerville et al. | |
| 3,080,293 A | 3/1963 | Koff | |
| 4,001,388 A | 1/1977 | Shell | |
| 4,014,335 A | 3/1977 | Arnold | |
| 4,057,619 A | 11/1977 | Higuchi et al. | |
| 4,123,206 A | 10/1978 | Dannelly | |
| 4,256,677 A | 3/1981 | Lee | |
| 4,317,743 A | 3/1982 | Chang | |
| 4,405,535 A * | 9/1983 | Raman et al. | 264/11 |
| 4,478,818 A | 10/1984 | Shell et al. | |
| 4,675,140 A | 6/1987 | Sparks et al. | |
| 4,764,317 A | 8/1988 | Anderson et al. | |
| 4,997,652 A | 3/1991 | Wong | |
| 5,019,302 A | 5/1991 | Sparks et al. | |
| 5,100,592 A | 3/1992 | Sparks et al. | |
| 5,143,662 A | 9/1992 | Chesterfield et al. | |
| 5,194,262 A | 3/1993 | Goldberg et al. | |
| 5,292,657 A | 3/1994 | Rutherford et al. | |
| 5,348,803 A | 9/1994 | Schlaemus et al. | |
| 5,505,967 A | 4/1996 | Geary et al. | |
| 5,578,314 A | 11/1996 | Cochrum et al. | |
| 5,601,761 A | 2/1997 | Hoffman et al. | |
| 5,643,594 A | 7/1997 | Dorian et al. | |
| 5,660,851 A | 8/1997 | Domb | |
| 5,665,428 A | 9/1997 | Cha et al. | |
| 5,697,976 A | 12/1997 | Chesterfield et al. | |
| 5,837,226 A | 11/1998 | Jungherr et al. | |
| 5,959,073 A | 9/1999 | Schlameus et al. | |
| 5,985,259 A | 11/1999 | Cagle et al. | |
| 6,001,387 A | 12/1999 | Cochrum | |
| 6,264,971 B1 | 7/2001 | Darougar et al. | |
| 6,297,228 B1 | 10/2001 | Clark | |
| 6,316,465 B1 | 11/2001 | Pershadsingh et al. | |
| 6,331,313 B1 | 12/2001 | Wong et al. | |
| 6,509,355 B1 | 1/2003 | Collier et al. | |
| 6,531,156 B1 | 3/2003 | Clark et al. | |
| 6,579,519 B2 | 6/2003 | Maitra et al. | |
| 6,630,135 B1 | 10/2003 | Cagle et al. | |
| 6,649,384 B2 | 11/2003 | Walsh et al. | |
| 6,746,635 B2 | 6/2004 | Mathiowitz et al. | |
| 6,881,482 B2 | 4/2005 | Vasisht | |
| 2002/0160109 A1 | 10/2002 | Yeo et al. | |
| 2003/0180352 A1 | 9/2003 | Patel et al. | |
| 2004/0121003 A1 | 6/2004 | Chickering, III et al. | |
| 2004/0127472 A1 | 7/2004 | Jerden et al. | |
| 2004/0265383 A1 | 12/2004 | Cui et al. | |
| 2005/0079138 A1 | 4/2005 | Chickering, III et al. | |

FOREIGN PATENT DOCUMENTS

WO    WO 00/48731    *    8/2000

OTHER PUBLICATIONS

Johnson, et al., "A New Method for Coating Glass Beads for Use in Gas Chromotography . . . ", 3 J. Gas Chrom. (1965), pp. 345-347.

(Continued)

*Primary Examiner*—Sharmila Gollamudi Landau
*Assistant Examiner*—Kevin S Orwig
(74) *Attorney, Agent, or Firm*—Grossman Tucker et al

(57) ABSTRACT

This invention is directed to an apparatus and method for producing microparticles comprising pharmacologically active agents and biodegradable polymers. The apparatus includes a spinning disk containing a reservoir in the center thereof and a flat inclined surface. The apparatus optionally includes serrations and/or a flat surface beneath the periphery of the disk that is parallel to the rotational axis of the disk. The invention is also directed to a method for producing microparticles containing pharmacologically active agents, using the spinning disk apparatus. Formulations containing ophthalmically active agents are provided. Formulations exhibiting zero order release rates are also described.

57 Claims, 12 Drawing Sheets

OTHER PUBLICATIONS

Babu, et al., "Analysis of Drop Formation at Conical Tips", 116[2] J. Colloid Interface Sci. (1987), pp. 350-372.

Franjione, et al., "The Art and Science of Microencapsulation", www.swri.org/3pubs/ttoday/summer95/microeng.htm (Apr. 25, 2005).

Friedlander, "AMD: New Therapeutic Strategies", www.rpbusa.org/library_content.php?document_id=111 (May 2, 2005).

Lai, et al., "Tracking RPE Transplants Labeled by Retroviral Gene Transfer with Green Fluorescent Protein", 40 Invest. Ophth. & Vis. Sci. 9(1999), pp. 2141-2162.

Stendahl, "Size Matters:Great Things Come in Tiny Packages", www.drugdeliverytech.com/cgi-bin/articles.cgi?idArticle=234 (Apr. 26, 2005).

* cited by examiner

FIGURES 4A-4C
(Prior Art)
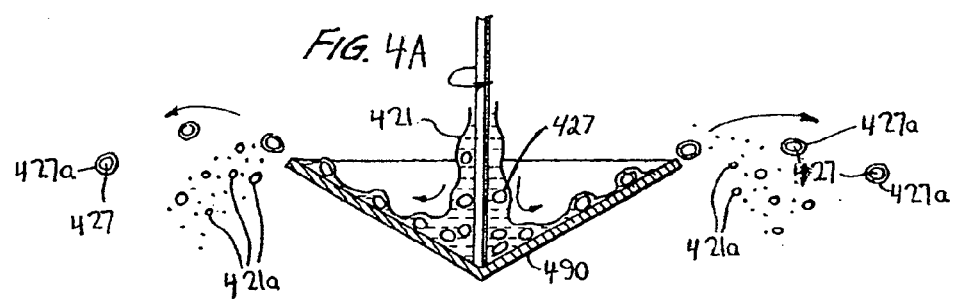
FIG. 4A
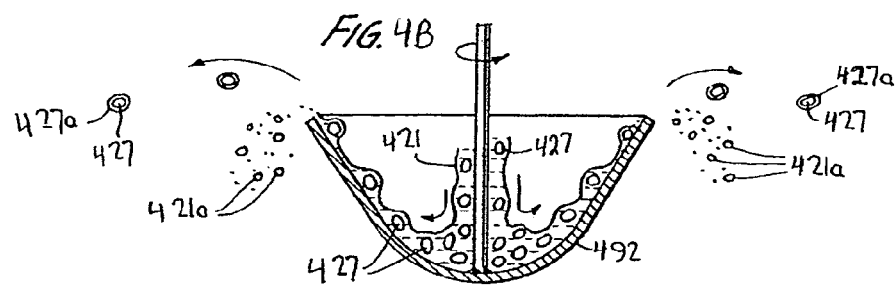
FIG. 4B
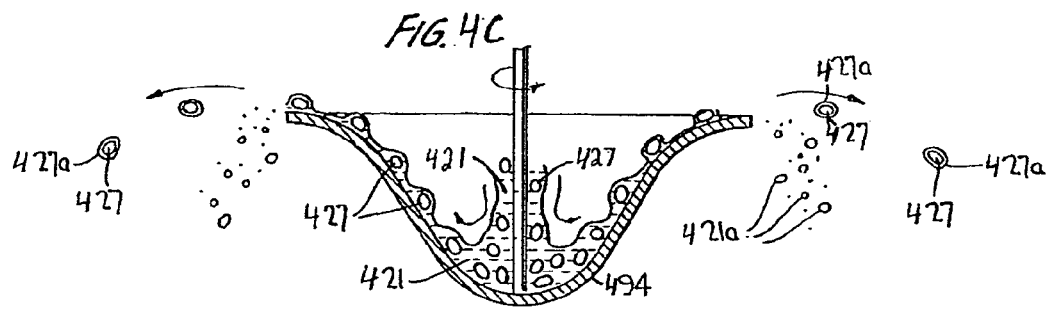
FIG. 4C

Microcapsules with reduced placebo particles. (50X magnification)

Microcapsules with improved coating uniformity. (200X magnification)

Microcapsules produced using conventional disk. (50X magnification)

Microcapsules produced using conventional disk. (200X magnification)

METHODS FOR PREPARING BIODEGRADABLE MICROPARTICLE FORMULATIONS CONTAINING PHARMACEUTICALLY ACTIVE AGENTS

FIELD OF THE INVENTION

The present invention relates to the sustained release of pharmaceutically (i.e., pharmacologically) active agents. The invention specifically relates to a method and apparatus for making microcapsules and microspheres containing pharmaceutically active agents, especially ophthalmic active agents.

BACKGROUND OF THE INVENTION

Pharmacologically active agents may be administered systemically, such as orally or intravenously, or locally, such as topically or subcutaneously. In either instance, it is often desirable to deliver to the targeted location a dosage of these agents that is no greater than that which may be metabolized immediately, as dosages in excess thereof may be unusable and/or harmful. This has traditionally required administration of the agents at regular time intervals, which can be laborious and/or impractical and can also lead to errors in administration.

As an alternative, pharmacologically active agent delivery systems have been developed whereby the active agent is delivered (preferably in a consistent, sustained-release amount) over a period of time. Specifically with regard to locally administered agents, sustained-release has been accomplished by utilizing microparticles containing the active agent and one or more pharmacologically inactive materials. Microparticles can be divided into "microspheres" and "microcapsules," which are different from each other. Microspheres usually refer to a monolithic type formulation in which the drug molecules are dispersed throughout a polymeric matrix. On the other hand, microcapsules refer to reservoir devices in which the drug core is surrounded by a continuous polymeric layer or shell. The drug core of a microcapsule may comprise the drug itself or a microsphere containing the drug.

The microparticles are delivered to the desired location and the active agent is released therefrom over an extended period of time. For ocular applications, the microparticles can be delivered, for example, by injection to the posterior segment of the eye using a designed cannula, or otherwise introduced as implants.

Release of the active agent from microspheres may involve melting, solvation, and/or biodegradation of the polymer matrix. In the case of microcapsules, the active agent must penetrate the shell to reach the target location. This may be accomplished by mechanical rupture, melting, dissolution, ablation, and/or biodegradation of the shell and/or diffusion of the active agent through the shell.

In particular, biodegradable materials, such as polymers, that form a matrix with and/or encapsulate the pharmaceutically active agents, can be employed as a sustained delivery system. By biodegradable, it is meant that the materials are degraded or broken down under physiological conditions in the body such that the degradation products are excretable or absorbable by the body. The use of biodegradable polymers can provide a sustained release of an active agent by utilizing the biodegradability of the polymer to control the release of the active agent thereby providing a more consistent, sustained level of delivery.

The prior art discloses several methods of producing microparticles, including by solvent extraction, low-temperature casting, coacervation, hot melting, interfacial cross-linking, interfacial polymerization, spray drying, supercritical fluid expansion, supercritical fluid antisolvent crystallization, and solvent evaporation. Solvent extraction involves the use of organic solvents to dissolve water-insoluble polymers. A drug in soluble or dispersed form is added to the polymer solution, and the mixture is then emulsified in an aqueous phase containing a surface-active agent. The organic solvent diffuses into the water phase facilitating precipitation of solid polymer microspheres. An example of this technology may be found in U.S. Pat. No. 4,389,330 (issued to Tice, et al.).

A process known as low-temperature casting has been utilized to produce microparticles. In this process, which is described in U.S. Pat. No. 5,019,400 (issued to Gombotz, et al.), a polymer is dissolved in a solvent together with an active agent that can be either dissolved in the solvent or dispersed in the solvent in the form of microparticles. The polymer/active agent mixture is atomized into a vessel containing a liquid non-solvent, and overlayed with a liquefied gas, at a temperature below the freezing point of the polymer/active agent solution. The cold liquefied gas or liquid immediately freezes the polymer droplets. As the droplets and non-solvent for the polymer are warmed, the solvent in the droplets thaws and is extracted into the non-solvent, resulting in hardened microspheres.

Coacervation is based on salting out or phase separation from a homogeneous polymer solution of hydrophilic polymers into small droplets of a polymer-rich, second liquid phase. When an aqueous polymer solution is partially dehydrated or desolvated by adding a strongly hydrophilic substance or a water-miscible, non-solvent, the water-soluble polymer is concentrated in water to form the polymer-rich phase. This is known as "simple" coacervation. If water-insoluble drug particles are present as a suspension or as an emulsion, the polymer-rich phase is formed on the drug particle surface to form a capsule under suitable conditions. In "complex" coacervation, the polymer-rich complex (coacervate) phase is induced by interaction between two dispersed hydrophilic polymers (colloids) of opposite electric charges. This process is described in numerous patents, including U.S. Pat. No. 2,800,457 (issued to Green, et al.).

A hot melt or congealing process has been described wherein an active agent is mixed with a polymer, which is melted at high temperatures. The admixture is then transferred to a centrifugal atomizer and the formed droplets cooled and collected. This process is described in U.S. Pat. No. 3,080,293 (issued to Koff). Alternatively, as described in U.S. Pat. No. 4,898,734 (issued to Mathiowitz, et al.), the active agent is mixed with the melted polymer, and the molten mixture is suspended in a non-miscible solvent, heated above the melting point of the polymer, and stirred continuously. Once the emulsion is stabilized, it is cooled until the core material solidifies.

Interfacial cross-linking may be employed if the polymer possesses functional groups that can be cross-linked by ions or multi-functional molecules. As described in U.S. Pat. No. 4,138,362, (issued to Vassiliades, et al.), for example, producing microparticles by interfacial cross-linking involves mixing a water-immiscible, oily material containing an oil-soluble, polyfunctional cross-linking agent, and an aqueous solution of a polymeric emulsifying agent. An oil-in-water emulsion is formed containing the polyfunctional cross-linking agent dispersed in the form of microscopic emulsion droplets in the aqueous continuous phase containing the emulsifying agent, and a solid capsule wall is formed by the cross-linking of the emulsifying agent by the polyfunctional cross-linking agent.

Interfacial polymerization requires monomers that can be polymerized at the interface of two immiscible substances to form a membrane. U.S. Pat. No. 4,119,565 (issued to Baatz, et al.) discloses a process for encapsulation wherein a polyfunctional compound is dissolved in a core material, or in an inert solvent or solvent mixture, and subsequently mixed with the core material. This homogeneous mixture is then introduced into a liquid phase immiscible therewith, for example water, which contains a material that catalyzes polymerization of the poly-functional compound.

Another known microparticle process is spray drying, wherein a solid forming material, such as a polymer, which is intended to form the bulk of the particle, is dissolved in an appropriate solvent to form a solution. Alternatively, the material can be suspended or emulsified in a non-solvent to form a suspension or emulsion. An active agent is then added and the solution is atomized to form a fine mist of droplets. The droplets then enter a drying chamber where they contact a drying gas. The solvent is evaporated from the droplets into the drying gas to solidify the droplets, thereby forming particles. The particles are then separated from the drying gas and collected. This process is described in U.S. Pat. No. 6,308,434 (issued to Chickering, III, et al.), and references disclosed therein.

Microparticle formation using supercritical fluid expansion involves the rapid dissolving of a solid material into a supercritical fluid solution at an elevated pressure and then rapidly expanding the solution into a region of relatively low pressure. This produces a molecular spray that is discharged into a collection chamber. The solvent is vaporized and pumped away, and the particles are collected. An example of this process is described in U.S. Pat. No. 4,734,451 (issued to Smith).

Supercritical antisolvent crystallization, as disclosed in U.S. Pat. No. 6,461,642 (issued to Bisrat, et al.), involves dissolving the active agent, and, optionally, one or more carrier materials in a first solvent, introducing the solution and a supercritical or subcritical fluid into an apparatus, wherein the fluid contains an anti-solvent (such as carbon dioxide) and a second solvent. The essentially crystalline particles formed contain the active agent in a solvated form. The particles may be further dried using a dry anti-solvent in a supercritical or subcritical state.

One widely utilized process employs solvent evaporation to form microparticles containing active agents. In a solvent evaporation process, the active agent and matrix material are dissolved in a volatile organic solvent that is ultimately removed by raising the temperature and/or lowering the pressure. The most widely utilized apparatus for forming microparticles via solvent evaporation incorporates a rotating device, often referred to as a spinning disk. The spinning disk process was originally described in U.S. Pat. No. 3,015,128, (issued on Jan. 2, 1962 to G. R. Somerville, Jr.), the disclosure of which that is germane to the spinning disk process is hereby incorporated by reference in its entirety to the extent not inconsistent with the disclosures in this Application.

Since the advent of the spinning disk technology, numerous modifications of the method and apparatus have been introduced; however, various problems associated therewith have not been alleviated. For example, broad particle size distributions are often obtained. Importantly, the narrower the particle size distribution, the more calculable and repeatable the dosage of active agents. In addition, "pure" coating material particles (placebo particles) are produced. This results in dosage dilution if the placebo particles are administered, or additional manufacturing costs if the placebo particles have to be separated from the active agent-containing microparticles. Furthermore, agglomeration of microparticles occurs, which further affects particle size distribution. What is needed is an apparatus and method for producing microparticles having narrow particle size distribution, reduced placebo formation, decreased agglomeration of particles, and improved product yield.

SUMMARY OF THE INVENTION

A spinning disk apparatus for producing microparticles having these desired properties is provided wherein the apparatus contains a substantially circular spinning disk comprising a substantially smooth annular disk surface comprising a substantially flat incline, wherein an outer peripheral edge thereof defines a first diameter and an inner peripheral edge thereof defines a second diameter, and wherein the area circumscribed by the inner peripheral edge includes a reservoir comprising a top portion thereof defined by the inner peripheral edge of the annular disk surface, and wherein the reservoir is partially defined by a third diameter, located between the bottom of the reservoir and the top portion of the reservoir, wherein the third diameter is greater than the second diameter. The spinning disk apparatus may comprise a substantially flat surface beneath the annular disk surface and proximate the outer peripheral edge thereof, wherein the substantially flat surface lies in a plane that is substantially parallel to the rotational axis of the spinning disk. In addition, the outer peripheral edge of the annular disk surface may comprise serrations.

A method for producing microparticles utilizing the above-described spinning disk apparatus is provided. In an embodiment thereof, microspheres are produced by combining an active agent with a matrix material to form a composition that is introduced to the reservoir of the spinning disk apparatus, and operating the apparatus to produce microspheres comprising the active agent and the matrix material. In another embodiment thereof, a method for producing microcapsules is also provided wherein microspheres are combined with a coating material and introduced to the reservoir of the spinning disk apparatus and operation thereof produces microcapsules comprising the microspheres coated with the coating material. The active agent may comprise a pharmacologically active agent and the matrix and coating materials may comprise biodegradable polymers.

Formulations comprising microparticles containing biodegradable polymers and an ophthalmically active agent are also provided. The ophthalmically active agent may comprise anecortave acetate; an alcohol form thereof, derivatives thereof, and combinations thereof. In an embodiment, the formulation comprises microspheres containing the ophthalmically active agent. In another embodiment, the formulation comprises microcapsules containing the ophthalmically active agent.

Formulations comprising microcapsules that when introduced to a living organism release a pharmacologically active agent at a substantially zero order rate are provided. The microcapsules comprise microspheres comprising a biodegradable polymer and containing more than about 15 wt. % of a pharmacologically active agent, and a biodegradable polymer coating material. In one aspect, the release of the pharmacologically active agent at a substantially zero order rate extends over a time period of at least about four weeks.

Microcapsules prepared by the methods described above are provided wherein the microcapsules, when introduced to a living organism, release a pharmacologically active agent at a substantially zero order rate. These microcapsules comprise a biodegradable polymer coating material over a microsphere core that comprises a biodegradable polymer and a pharmacologically active agent. The microsphere contains more than about 15 wt. % of the pharmacologically active agent. In one aspect, the release of the pharmacologically active agent at a substantially zero order rate extends over a time period of at least about four weeks.

BRIEF DESCRIPTIONS OF THE DRAWINGS

For a more complete understanding of the present invention, and the advantages thereof, reference is now made to the following descriptions taken in conjunction with the accompanying drawings, in which:

FIG. 4A illustrates schematically a spinning disk in accordance with prior art technology;

FIG. 4B illustrates schematically a spinning disk in accordance with prior art technology;

FIG. 4C illustrates schematically a spinning disk in accordance with prior art technology;

DETAILED DESCRIPTION

Figure 1:
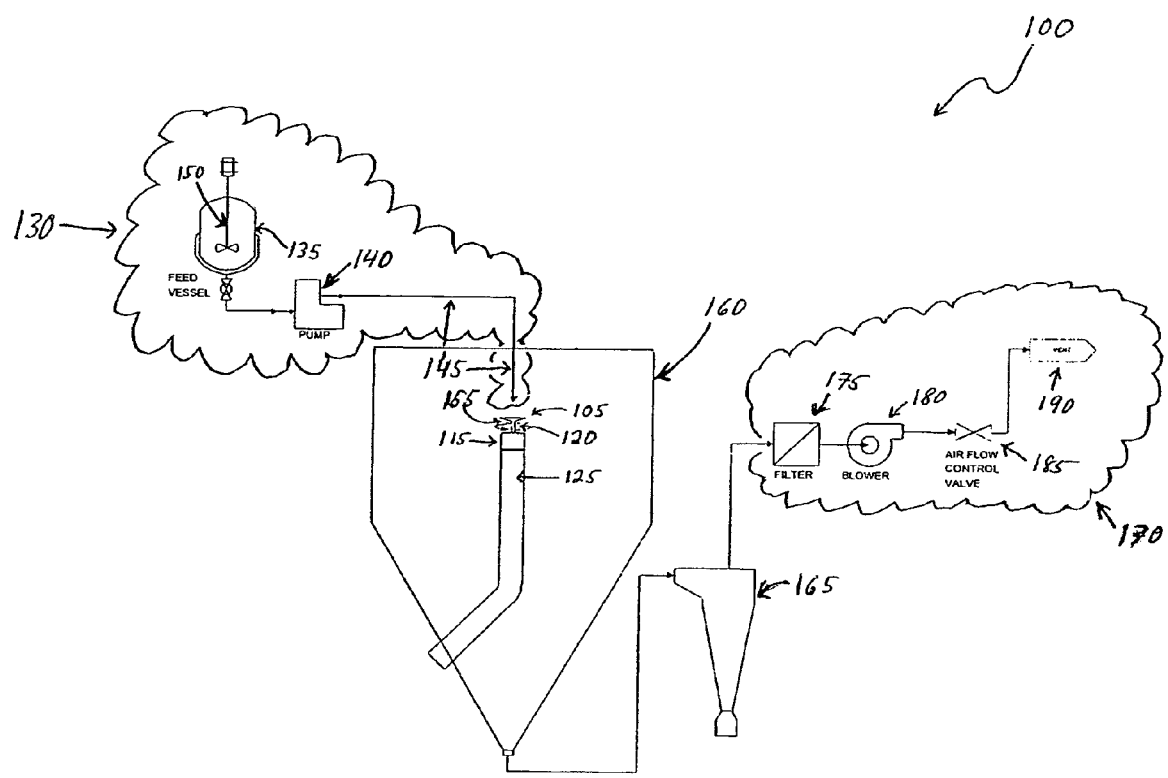
FIG. 1 illustrates schematically a spinning disk apparatus in accordance with an embodiment of the present invention.

FIG. 1 depicts a spinning disk apparatus 100 in accordance with an embodiment of the present invention. Spinning disk apparatus 100 includes a spinning disk 105, which is coupled to stirrer motor 115 by connecting rod 120. Spinning disk 105 is typically substantially circular and can have a diameter of between about 10 mm and about 300 mm. As will be described in greater detail below, spinning disk 105 may have a variety of surface features and comprise various geometries. Stirrer motor 115 is supported within spinning disk apparatus 100 by a motor mounting frame 125. Stirrer motor 115, which may be driven hydraulically, pneumatically or electrically, is adapted to rotate spinning disk 105 via connecting rod 120. Stirrer motor 115 includes a speed control system (not shown) adapted to rotate spinning disk 105 at various speeds, such as from about 60 rpm to about 25,000 rpm.

Spinning disk apparatus 100 also includes a sample delivery system 130, that includes one or more feed vessels 135, one or more fluid pumps 140, and a fluid delivery system 145. Fluid delivery system 145 typically comprises a tube through which the materials to be processed within disk apparatus 100 are introduced onto spinning disk 105. Fluid pumps 140 are typically adapted to deliver fluids from feed vessels 135 to spinning disk 105 via fluid delivery system 145 at flow rates of about 0 to about 750 g/min. Feed vessels 135 include one or more agitation means 150 (such as a stirrer) adapted to facilitate mixing of materials introduced into feed vessels 135 and may optionally include a temperature control system (not shown) adapted to control the temperature of materials contained therein.

Proximate spinning disk 105 is a heating unit 155, which may be in contact with or integral to spinning disk 105 as shown, or alternatively, disposed in close, non-contacting proximity thereto. Suitable heating units 155 include, but are not limited to, capacitance heaters, impedance heaters, liquid circulation heaters, hot air guns, and the like.

Spinning disk apparatus 100 includes a process chamber 160, which hermetically seals a space surrounding spinning disk 105 and is operably connected to a gas source (not shown) adapted to maintain the environment within process chamber 160 under a controlled atmosphere. Process chamber 160 may optionally include a vacuum source (not shown) adapted to control the pressure within process chamber 160. The gaseous environment maintained within process chamber 160 may comprise air or some inert gas or gases which are supplied to the process chamber 160 by a gas feed means (not shown). Process chamber 160 may comprise thermally controllable internal surfaces, comprising a material such as, but not limited to, jacketed stainless steel. Alternatively or additionally, process chamber 160 may include internal surfaces having low thermal conductivity, such as, but not limited to, plastic. In one embodiment, the plastic utilized is high density polyethylene (HDPE), however, the invention is not limited to this material and other similarly suitable materials may be employed.

Process chamber 160 may include a cone bottom tank containing internal surfaces comprising the abovementioned materials. Spinning disk apparatus 100 additionally can include a sample collection system 165, which is operably connected to process chamber 160. Suitable sample collection systems 165 include, but are not limited to, cyclone separators. Operably connected to sample collection system 165 may be an evacuation system 170, which can include one or more filters 175, one or more blowers 180, one or more air flow control valves 185, and one or more vents 190. A cyclone separator comprising sample collection systems 165 may also comprise a thermally controllable internal surface, such as, but not limited to, jacketed stainless steel, and/or surfaces having low thermal conductivity, such as, but not limited to, plastic. In one embodiment, the plastic utilized is high density polyethylene (HDPE), however, the invention is not limited to this material and other similarly suitable materials may be employed.

In addition as will be described in more detail below, sample collection system 165 may be run continuously. The surfaces of spinning disk apparatus 100 that contact the microparticles produced therein, including but not limited to, surfaces of process chamber 160 and sample collection systems 165, may be thermally controlled by temperature control devices (not shown) to reduce particle agglomeration.

Figure 2:
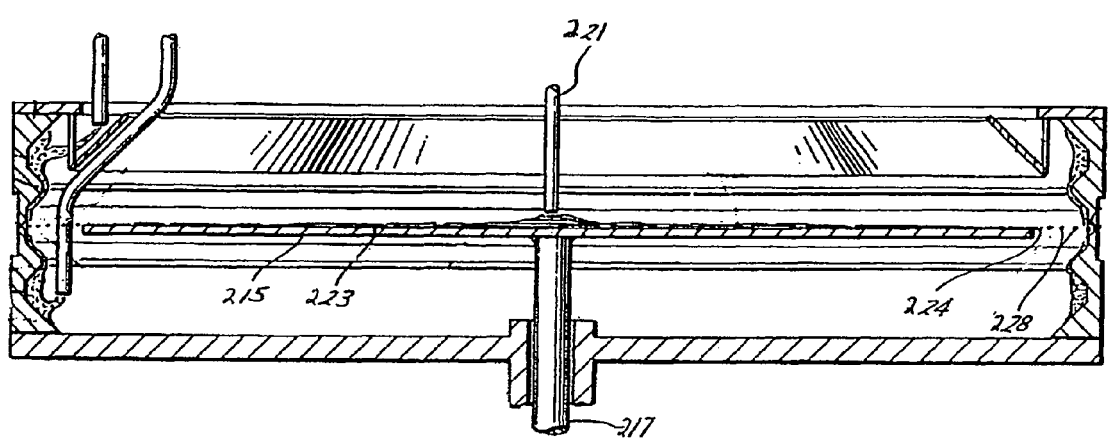
FIG. 2 illustrates schematically a spinning disk in accordance with prior art technology.

FIGS. 2-6 depict spinning disks in accordance with prior art technology. FIG. 2 shows a substantially flat spinning disk as disclosed in U.S. Pat. No. 3,015,128 (issued to Somerville, Jr.), with which microparticles are produced by introducing materials through line 221 onto the surface of 223 of spinning disk 215 proximate the center thereof. Spinning disk 215 is rotated by drive shaft 217 using a motor (not shown) operably connected thereto, thereby urging the materials introduced onto the surface 223 of spinning disk 215 radially outwardly along the surface 223 to the peripheral edge 224 of spinning disk 215 where the materials are trajected outwardly from random points and thereby separated into discrete particles 228.

Figure 3:
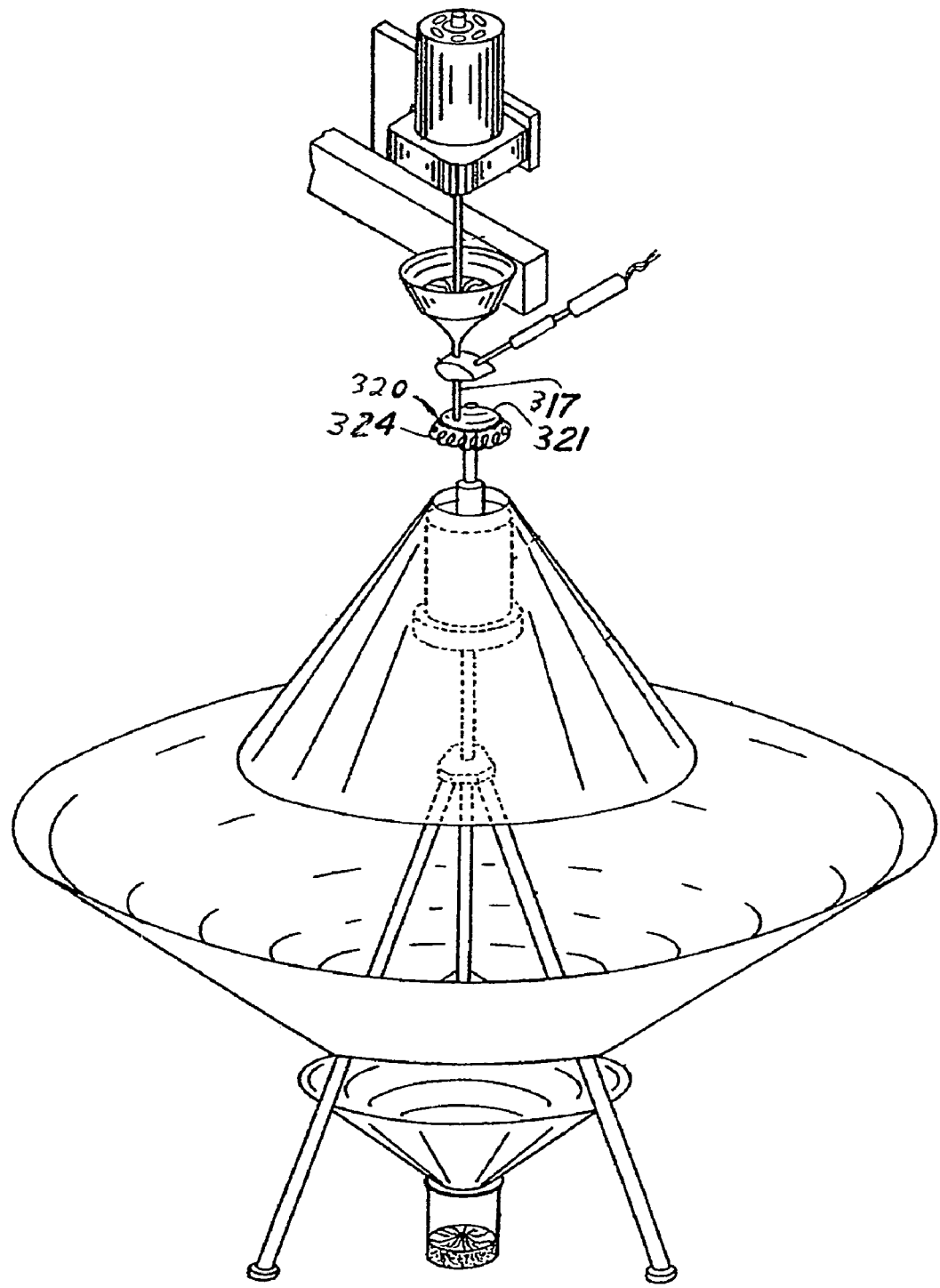
FIG. 3 illustrates schematically a spinning disk in accordance with prior art technology.

FIG. 3 shows a prior art spinning disk containing teeth around the periphery thereof, as disclosed in U.S. Pat. No. 4,256,677 (issued to Lee). As depicted therein, the materials fed through outlet 317 onto the surface of rotating disk 321 which contains teeth 320 around the periphery thereof. Outlet 317 is disposed such that the materials introduced thereby contact the surface of toothed disk 321 near the periphery thereof. Toothed disk 321 is convex with respect to the introduction of materials via outlet 317 and is heated using heating element 324 disposed proximate the peripheral edge of toothed disk 321. Using conventional spinning disk methodology as previously described, microparticles are thereby produced.

FIGS. 4A-4C depict prior art spinning disks having a concave geometry, as disclosed in U.S. Pat. No. 4,675,140 (issued to Sparks, et al.). FIG. 4A shows an angled spinning disk 490, onto which is introduced molten or dissolved coating material 421 and core material 427, which may comprise a solid particles or liquid droplets. Using conventional spinning disk methodology as previously described, microparticles comprising core particles 427 with a liquid coating layer 427a, and droplets 421a of excess unused coating material 421, are thereby produced. FIG. 4B shows a parabolic spinning disk 492 and FIG. 4C shows a sigmoidal spinning disk 494, which form microparticles as described above.

Figure 5:
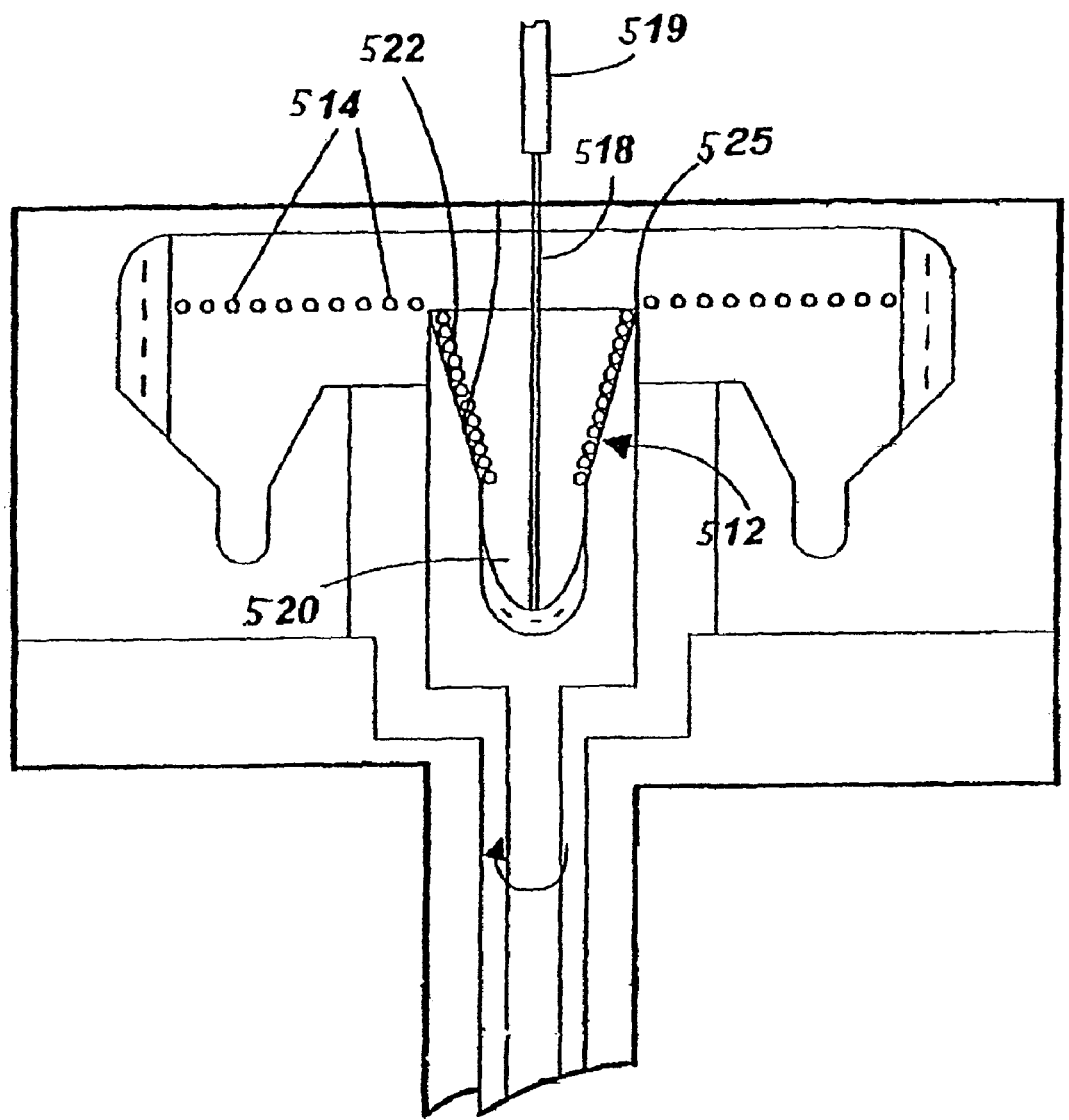
FIG. 5 illustrates schematically a spinning disk in accordance with prior art technology.

FIG. 5 shows a prior art spinning apparatus having a cup-shaped rotational member, as disclosed in U.S. Pat. No. 5,643,594 (issued to Dorian, et al.). As described therein, the cup 512 receives a supply mixture 518 of a suspension of particles in a solution of a coating polymer, via a conduit or tube 519. The cup 512 includes a mixing chamber 520, which extends into an upwardly diverging, conically shaped sidewall 522, and which terminates into an upper rim or edge 525. The cup 512 is designed to project the beads 514 radially outwardly along a generally horizontal trajectory by employing conventional spinning disk methodology as previously described.

Figure 6:
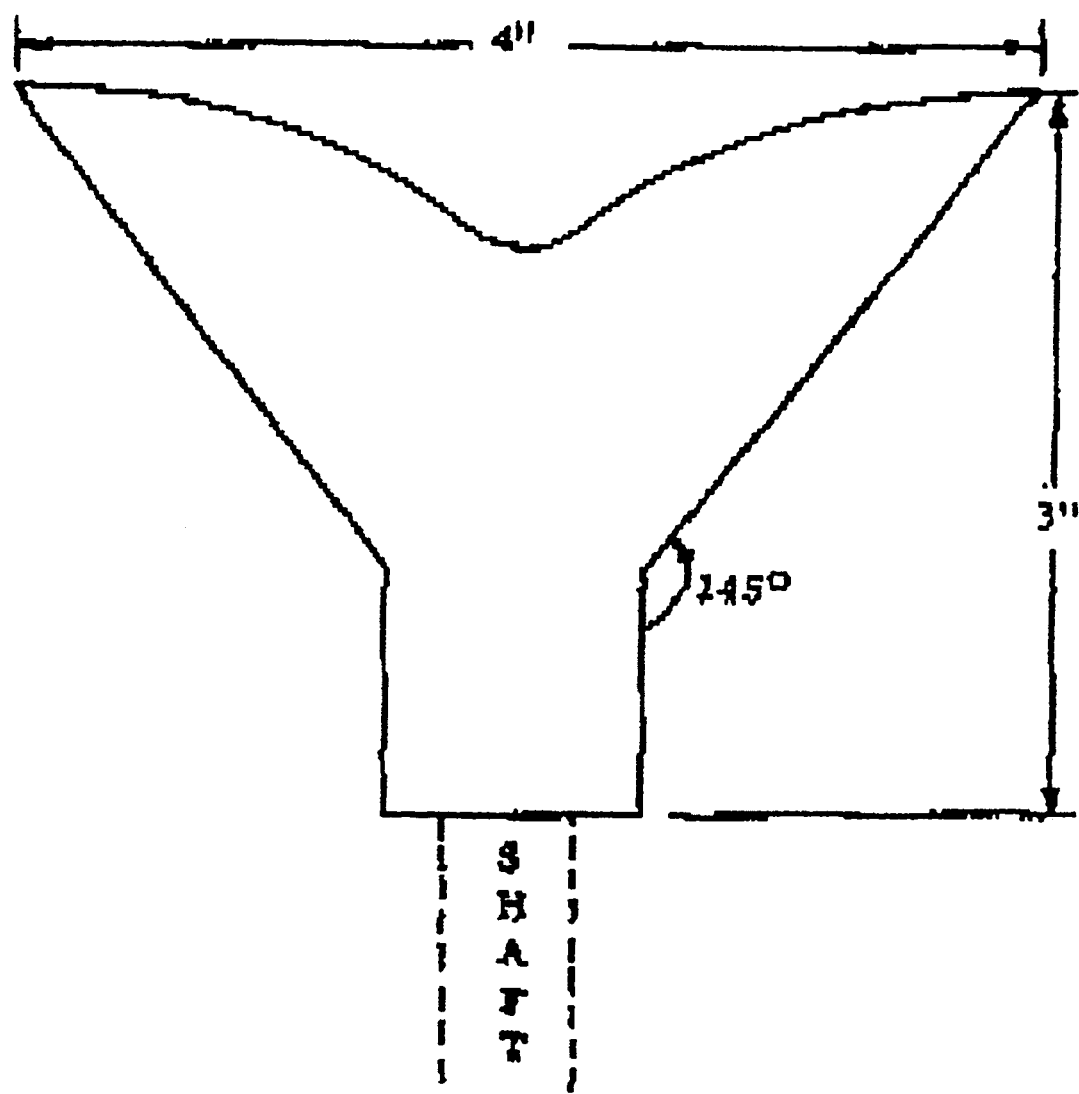
FIG. 6 illustrates schematically a conventional spinning disk in accordance with prior art technology.

FIG. 6 shows a conventional prior art spinning apparatus ("conventional disk") as described in Johnson, D. E., et. al, "A New Method for Coating Glass Beads for Use In Gas Chromatography of Chloropromazine and Its Metabolites," *J. Gas Chrom.*, 3, 345-47 (1965), the disclosure of which that is germane to the spinning disk is hereby incorporated by reference in its entirety to the extent not inconsistent with the disclosures in this Application. The conventional disk depicted therein includes a concave geometry in which the disk surface curves sigmoidally from the center to the periphery thereof. For purposes of generally disclosing features and advantages of the present invention as discussed below, the conventional disk described in the above cited reference constitutes the standard for comparison.

Figure 7:
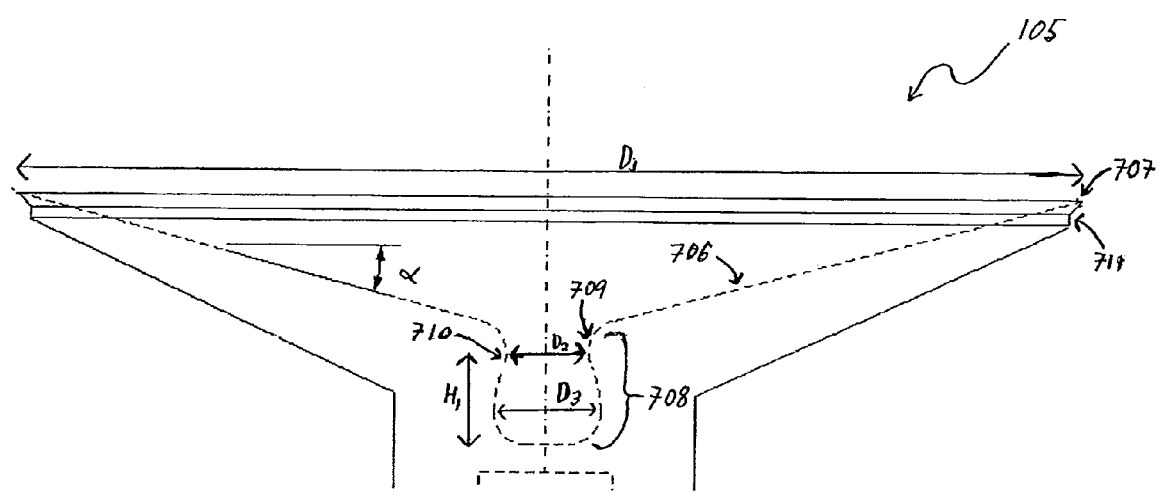
FIG. 7 illustrates schematically a side view of a spinning disk in accordance with an embodiment of the present invention.

FIG. 7 depicts a spinning disk encompassing one embodiment of the present invention. Spinning disk 105 includes a substantially smooth annular surface 706 on what is defined herein as the top face of spinning disk 105. Spinning disk 105 comprises an outer peripheral edge 707. Spinning disk 105 also includes a reservoir 708 partially defined by an inner peripheral edge 709 of spinning disk 105 and disposed in the center thereof. Reservoir 708 has a vertical displacement $H_1$ that can be between about 5 mm and about 20 mm. A diameter $D_3$ defines a maximum width of reservoir 708, while a diameter $D_2$ defines a minimum width of reservoir 708. Diameter $D_3$ can be in the range of about 1 mm to about 20 mm. Diameter $D_2$ can be in the range of about 1 mm to about 20 mm. The diameter $D_2$ is disposed closer to the open end of reservoir 708 than is diameter $D_3$. That is to say, reservoir 708 has an opening that is narrower than at least some cross-sectional area below the opening. This geometry produces a lip 710 at the top of reservoir 708.

Annular surface 706 has diameter $D_1$ that can be between about 10 mm to about 300 mm. Annular surface 706 comprises a flat incline that defines a fixed angle α, which may range from about 2 degrees to about 85 degrees, preferably from about 5 degrees to about 45 degrees, and more preferably from about 15 degrees to about 30 degrees. An additional optional feature of spinning disk 105 is a substantially flat surface 711 substantially parallel to the disk rotational axis beneath annular surface 706 proximate outer peripheral edge 707. The substantially flat surface 711 may range from about 1 mm to about 10 mm in length. The inclusion of surface 711 having this geometry assists in more accurately machining disk 105 by providing a second reference surface to aid in re-fixturing and significantly reducing chatter during the disk-machining process.

Spinning disk 105 may be composed of any suitable material that can be fabricated to meet the specifications therefor, such as a metallic or synthetic material. In certain embodiments spinning disk 105 was fabricated from 304 or 316 stainless steel, however the present invention is not limited to disks comprising these materials. Annular surface 706 and the surface of reservoir 708 may be ground and polished to a mirror finish; however, one skilled in the art would understand that the surface characteristics of a spinning disk affect the performance thereof and may be optimized to achieve desired results.

Figure 8:
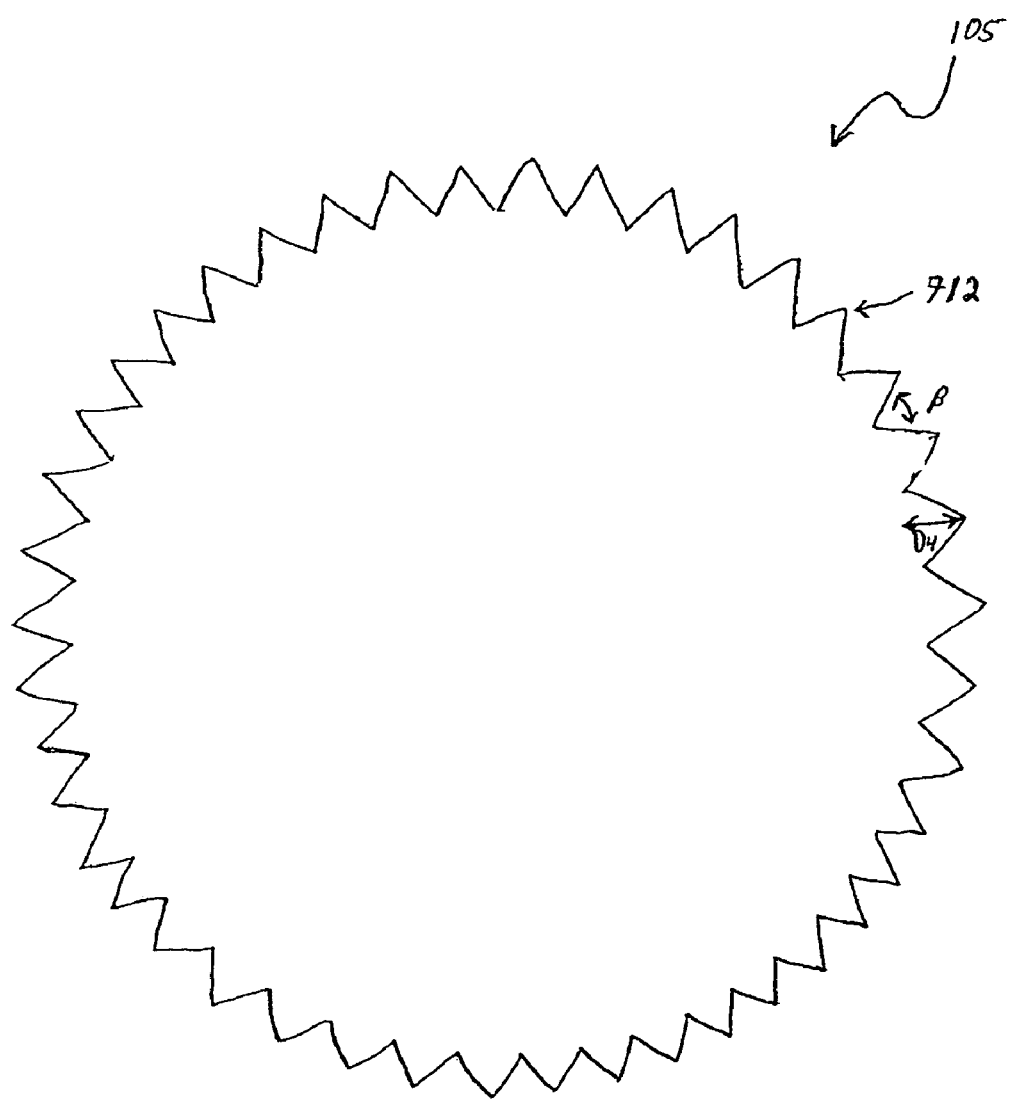
FIG. 8 illustrates schematically a top view of one embodiment of the spinning disk depicted in FIG. 7.

As shown in FIG. 8, Spinning disk 105 may optionally include serrations ("teeth") 712 comprising outer peripheral edge 707. Teeth 712 may define an angle β, which may range from about 145 degrees to about 10 degrees, preferably from about 105 degrees to about 15 degrees, and more preferably from about 65 degrees to about 20 degrees. However, one skilled in the art would understand that the angle β would affect the performance of a spinning disk and could be optimized to achieve desired results. Teeth 712 may define a horizontal displacement $D_4$ of between about 0 μm and about 5,000 μm.

The apparatus described in FIGS. 1, 7, and 8 may be employed to produce microparticles in accordance with embodiments of the present invention. In one aspect, the apparatus is utilized to produce microspheres. In an embodiment, the microspheres are produced by dispersing a pharmacologically active agent in solutions containing a biodegradable polymer. Referring again to FIG. 1, the solution is prepared by introducing a biodegradable polymer and a solvent to feed vessel 135. Suitable biodegradable polymers include, but are not limited to, poly lactic acids, (PLA), poly glycolic acids (PGA), poly lactic-glycolic acids (PLGA), polycaprolactone (PCL), poly orthoesters, polyanhydrides, polyesters, cellulosics, triglycerides (such as Sterotex K and Sterotex NF), poly ethylene glycols (PEG), and combinations thereof. Suitable solvents include any material in which the biodegradable polymer will dissolve. Such solvents include, but are not limited to, methanol, ethanol, methylene chloride, chloroform, ethyl acetate, acetone, and combinations thereof. Although less volatile solvents may be used in accordance with the invention, it is a particular feature of the present invention that lower boiling solvents may be employed.

The pharmacologically active agent is thereupon dispersed in the biodegradable polymer solution by introduction thereof into feed vessel 135. Suitable pharmacologically active agents that may be used to advantage with the present invention include, but are not limited to, ophthalmically active agents, angiogenic inhibitors, anti-inflammatory agents (steroidal and non-steroidal), tyrosine kinase inhibitors, anti-infectives, (e.g., antibiotics, antivirals, and antifungals), anti-allergic agents (e.g., antihistamines and mast cell stabilizers), cyclooxygenase inhibitors, (e.g., Cox I and Cox II inhibitors), decongestants, anti-glaucoma agents, (e.g., adrenergics, beta.-adrenergic blocking agents, alpha-adrenergic agonists, parasypathomimetic agents, cholinesterase inhibitors, carbonic anhydrase inhibitors, and prostaglandin analogs), phosphatidyl-inositol kinase inhibitors, gama-aminobutyric acid and derivatives thereof (including Gabapentin and Pregabalin), antioxidants, nutritional supplements, agents for the treatment of cystoid macular edema (e.g., non-steroidal anti-inflammatory agents), agents for the treatment of age related macular degeneration (ARMD), (e.g., angiogenesis inhibitors and nutritional supplements), agents for the treatment of herpetic infections and cytomegalovirus (CMV) ocular infections, agents for the treatment of proliferative vitreoretinopathy (e.g., antimetabolites and fibrinolytics), wound modulating agents (e.g., growth factors), anti-metabolites, neuroprotective drugs (e.g., eliprodil), angiostatic steroids for the treatment of diseases or conditions of the posterior segment of the eye, (e.g., ARMD, choroidal neovascularization (CNV), retinopathies, retinitis, uveitis, macular edema, and glaucoma), and combinations thereof. One specific pharmacologically active agent suitable for employment with the present invention is the ophthmalically active agent anecortave acetate (4,9(11)-pregnadien-17α,21-diol-3,20-dione-21-acetate), which may also be utilized in its alcohol form (4,9(11)-pregnadien-17α,21-diol-3,20-dione), or in other pro-drug derivative forms.

Once the dispersion or solution containing the pharmacologically active agent, the biodegradable polymer, and the solvent is prepared, the dispersion is transferred to the top face of a rotating spinning disk 105 using fluid pump 140 and fluid delivery system 145. While the dispersion may be introduced onto the spinning disk 105 on any portion thereof (including annular surface 706), it is a feature of the present invention that the dispersion may be introduced into reservoir 708. Prior to and throughout the microsphere manufacture, process chamber 160 is maintained at conditions conducive to controlled evaporation of the solvent from the dispersion. This is accomplished by controlling the temperature of annular surface 706 and reservoir 708 (using heating unit 155) and the temperature and/or pressure of the process chamber 160 (using a vacuum source not shown) such that the evaporation rate of the solvent enhances the production of microspheres. One skilled in the art would appreciate the affects of temperature and pressure on solvent evaporation (and, hence, microsphere production) and understand that conditions may be optimized to produce the desired materials.

Upon introduction of the dispersion or solution into reservoir 708, the centrifugal force transferred to the dispersion from rotating spinning disk 105 urges the dispersion as a liquid film up the interior surface of reservoir 708. Prior to the liquid film advancing outward onto the flat angled portion of annular surface 706 of spinning disk 105 toward the outer peripheral edge 707, it must traverse the lip 710 of reservoir 708. It is a feature of the present invention that the lip 710 is disposed between of reservoir 708 and the flat angled portion of annular surface 706 extending to the outer peripheral edge 707. Once the liquid film has propagated beyond lip 710, the dispersion becomes more viscous as the solvent is evaporatively removed therefrom. It would be understood by one skilled in the art that the rotation speed of spinning disk 105, in contemplation of the composition of the dispersion and the environmental conditions of process chamber 160, may be optimized to achieve the desired microsphere production.

The materials in the dispersion or solution can be atomized by being rotatively urged beyond the outer peripheral edge 707 and controllably ejected from the edge of spinning disk 105. Solidification of the atomized material as it falls to the bottom of process chamber 160 results in the formation of microspheres comprising the pharmacologically active agent and the biodegradable polymer. The microspheres so produced are collected using sample collection system 165. Microspheres having a diameter of about 1 μm to about 2,500 μm may be produced by this process. The microspheres so produced may comprise about 0.0001 wt. % to about 99 wt. % active agent, preferably about 0.001 wt. % to about 55 wt. % active agent, and more preferably about 0.01 wt. % to about 30 wt. % active agent.

In another embodiment of the present invention, microspheres are produced using a hot melt process (as generally described in U.S. Pat. No. 3,080,293 (issued to Koff)) that employs the apparatus of the present invention. In this embodiment, the biodegradable polymer is introduced to feed vessel 135 and melted or partially melted therein. Once the biodegradable polymer exists in the desired molten or partially molten state, the pharmacologically active agent is introduced thereto. As previously described, the dispersion can then be introduced to the reservoir 708 of rotating spinning disk 105 via fluid delivery system 145. The centrifugal force urges the dispersion as a liquid film up the interior surface of reservoir 708 and beyond the lip 710 of reservoir 708. The dispersion can be maintained in a molten or partially molten state by the temperature of annular surface 706 as it propagates outward to outer peripheral edge 707. The dispersion is rotatively ejected from spinning disk 105 and congeals as microspheres as it falls to the bottom of process chamber 160. The microspheres so produced can be collected using sample collection system 165. Microspheres having a diameter of about 1 μm to about 2,500 μm may be produced by this process. The microspheres so produced may comprise about 0.0001 wt. % to about 75 wt. % active agent, preferably about 0.001 wt. % to about 45 wt. % active agent, and more preferably about 0.01 wt. % to about 30 wt. % active agent.

In additional embodiments of the present invention, microspheres may be produced comprising core materials other than pharmacologically active agents. Thus, the apparatus of the present invention may be employed to produce microspheres suitable for introduction into living organisms wherein the sustained release materials do not cause pharmacologic or pathologic responses in vivo. Examples of such materials include, but are not limited to, dyes, radioactive compounds, imaging agents, quantum dots, contrast agents, and combinations thereof. Further, microspheres produced according to the present invention may comprise agents that are designed to be non-physiologically active ex vivo. Examples include, but are not limited to, ultraviolet blocking or absorbing compounds, deodorants or antiperspirants, emollients, cosmetics, and combinations thereof. In addition, microspheres produced according to the present invention may comprise matrix materials other than biodegradable polymers. Suitable materials include, but are not limited to, waxes, lipids, oils, gums, resins, cellulose, starches, non-biodegradable polymers, and combinations thereof.

In another aspect of the present invention, microcapsules comprising a coated microsphere can be produced. The formation of microcapsules involves applying an over-coat to microspheres utilizing the apparatus of the present invention. In an embodiment, microcapsule production according to the present invention involves applying a biodegradable over-coat to microspheres comprising a pharmacologically active agent and biodegradable polymer matrix. In this embodiment, a solution comprising a coating material and a solvent can be prepared in feed vessel 135. Suitable solvents include any material in which the coating material will dissolve but in which the microspheres are substantially insoluble. Such solvents include, but are not limited to, methanol, ethanol, methylene chloride, chloroform, ethyl acetate, acetone, and combinations thereof. Although less volatile solvents may be used in accordance with the invention, it is a feature of the present invention that lower boiling solvents may be employed. It is also a feature of this invention that the solvent utilized for microcapsule formation may be one incapable of extracting significant amounts of the active agent from the microsphere matrix. Suitable coating materials include, but are not limited to, poly lactic acids, (PLA), poly glycolic acids (PGA), poly lactic-glycolic acids (PLGA), polycaprolactone (PCL), poly orthoesters, polyanhydrides, polyesters, cellulosics, triglycerides (such as Sterotex K and Sterotex NF), poly ethylene glycols (PEG), and combinations thereof.

A microsphere comprising a pharmacologically active agent and a biodegradable polymer can be dispersed in the coating material solution. The dispersion thus formed can be introduced as previously described with reference to microsphere production into reservoir 708 of spinning disk 105 via fluid delivery system 145. As described above, the centrifugal force transferred to the dispersion from rotating spinning disk 105 can urge the dispersion as a liquid film up the interior surface of reservoir 708 beyond the lip 710. As described above, once the liquid film has propagated beyond lip 710, the dispersion becomes more viscous as the solvent is evaporatively removed therefrom. It would be understood by one skilled in the art that the rotation speed of spinning disk 105, in contemplation of the composition of the dispersion and the environmental conditions of process chamber 160, may be optimized to achieve the desired microcapsule production.

The materials in the dispersion can be atomized by being rotatively urged beyond outer peripheral edge 707 and ejected from spinning disk 105. Solidification of the atomized material as it falls to the bottom of process chamber 160 results in the formation of microcapsules comprising an outer layer of the biodegradable coating material over the microsphere core. The microcapsules so produced can be collected using sample collection system 165. Microcapsules having a diameter of about 1 μm to about 2,500 μm may be produced by this process. Microcapsules so produced have a coating comprised of about 0.002 vol. % to about 96 vol. %, preferably about 0.003 vol. % to about 50 vol. %, and more preferably about 0.004 vol. % to about 5 vol. %. The microcapsules so produced may comprise about 0.0001 wt. % to about 99 wt. % active agent, preferably about 0.001 wt. % to about 50 wt. % active agent, and more preferably about 0.01 wt. % to about 30 wt. % active agent.

In an additional embodiment, microencapsulation utilizing the apparatus of the present invention may comprise a hot melt process. In this embodiment, a biodegradable polymer coating material is introduced to feed vessel 135 and melted or partially melted therein. Once the coating material exists in the desired molten or partially molten state, a microsphere comprising a pharmacologically active agent and a biodegradable polymer is introduced thereto. As previously described, this dispersion is then introduced to the reservoir 708 of rotating spinning disk 105 via fluid delivery system 145. The centrifugal force urges the dispersion as a liquid film up the interior surface of reservoir 708 and beyond the lip 710 of reservoir 708. The dispersion is maintained in a molten or partially molten state by the temperature of annular surface 706 as it propagates outward to outer peripheral edge 707. The dispersion is rotatively ejected from spinning disk 105 and congeals as microcapsules comprising an outer layer of the biodegradable coating material over the microsphere core as it falls to the bottom of process chamber 160. The microcapsules so produced are collected using sample collection system 165. Microcapsules having a diameter of about 1 μm to about 2,500 μm may be produced by this process. Microcapsules so produced have a coating comprised of about 0.002 vol. % to about 96 vol. %. The microcapsules so produced may comprise about 0.0001 wt. % to about 99 wt. % active agent, preferably about 0.001 wt. % to about 50 wt. % active agent, and more preferably about 0.01 wt. % to about 30 wt. % active agent.

Embodiments of the present invention encompass microcapsule production utilizing the apparatus described herein. Microspheres employed to produce microcapsules according to the present invention may be produced using the herein described apparatus as disclosed above, or produced by another suitable process. In addition, microspheres encapsulated according to the present invention may comprise active agents that are non-pharmacologically active and/or matrix materials that do not comprise biodegradable polymers, such as the microspheres previously described herein. In additional embodiments, microcapsule production may be achieved in accordance with the present invention whereby the coating material does not comprise a biodegradable polymer. Suitable materials include, but are not limited to, waxes, lipids, oils, gums, resins, cellulose, starches, non-biodegradable polymers, and combinations thereof.

The following Examples are provided to demonstrate particular embodiments of the present invention. It should be appreciated by those of skill in the art that the methods disclosed in the Examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

Example 1

In one embodiment of the microsphere manufacturing process described above, 312 g of an 8% poly lactide-co-glycolide (PLGA) 50:50 solution in 60:40 acetone/methylene chloride was prepared in feed vessel 135. To this solution was added 9.7 g of anecortave acetate, and the resulting dispersion was transferred at a rate of about 120 g/min. via fluid delivery system 145 into the reservoir 708 of a spinning disk 105 having a diameter of about 76.2 mm, rotating at a rate of about 3,000-4,000 rpm. Utilizing a process chamber 160 comprising an internal surface of high-density polyethylene (HDPE), microspheres were formed by evaporative removal of the solvent with an outlet temperature of the process chamber 160 of about 48-50° C. An 88% yield (30.6 g) of microspheres was collected as a free-flowing powder using a cyclone separator.

Comparative Example 1

In an example comparable to Example 1 above, a stainless steel process chamber 160 was used instead of the plastic, less thermally conductive material. Therein, 250 grams of an 8% poly lactide-co-glycolide (PLGA) 50:50 solution in 60:40 acetone/methylene chloride was prepared in feed vessel 135. To this solution was added 7.8 g of anecortave acetate, and the resulting dispersion was transferred at a rate of about 125 g/min. via fluid delivery system 145 into the reservoir 708 of a spinning disk 105 having a diameter of about 76.2 mm, rotating at a rate of about 3,000-4,000 rpm. The microspheres were formed by evaporative removal of the solvent with an outlet temperature of the stainless steel process chamber 160 of 48-50° C. The microspheres agglomerated on the sides of stainless steel process chamber 160 and no discrete microspheres were collected.

Example 2

In an embodiment of the microsphere manufacturing process described herein, 200 g of 5% poly lactide-co-glycolide (PLGA) 90:10 solution in acetone was prepared in feed vessel 135. To this solution was added 6.7 g of anecortave acetate. The resulting dispersion was transferred at a rate of about 180 g/min. via fluid delivery system 145 into the reservoir 708 of a spinning disk 105 having a diameter of about 76.2 mm, rotating at a rate of about 4,000-5,000 rpm. Utilizing a process chamber 160 comprising an internal surface of high-density polyethylene (HDPE), the microspheres were formed by evaporative removal of the acetone with an outlet temperature of the process chamber 160 of about 45° C. A 90% yield (15.0 g) of microspheres was collected as a free-flowing powder using a cyclone separator.

Example 3

In an embodiment of the microsphere manufacturing process described herein, 200 g of 5% poly lactide-co-glycolide (PLGA) 90:10 solution in acetone was prepared in feed vessel 135. To this solution was added 0.5 g of polyethylene glycol (PEG 400) and 3.5 g of anecortave acetate. The resulting dispersion was transferred at a rate of about 200 g/min. via fluid delivery system 145 into the reservoir 708 of a spinning disk 105 having a diameter of about 76.2 mm, rotating at a rate of about 4,000-5,000 rpm. Utilizing a process chamber 160 comprising an internal surface of high-density polyethylene (HDPE), the microspheres were formed by evaporative removal of the acetone with an outlet temperature of the process chamber 160 of about 45° C. A 77% yield (10.8 g) of microspheres was collected as a free-flowing powder using a cyclone separator.

Example 4

In an embodiment of the microsphere manufacturing process described herein, 100 g of 5% poly lactide-co-glycolide (PLGA) 75:25 solution in acetone was prepared in feed vessel 135. To this solution was added 0.56 g of Isopropyl (Z)-7-[(1R,2R,3R,5R)-5-chloro-3-hydroxy-2-[(3R)-[3-cyclohexyl-3-hydroxy]-1-propyl]cyclopentyl]-5-heptenoate. The resulting solution was transferred at a rate of about 85 g/min. via fluid delivery system 145 into the reservoir 708 of a spinning disk 105 having a diameter of about 76.2 mm, rotating at a rate of about 5,500 rpm. Utilizing a process chamber 160 comprising an internal surface of high-density polyethylene (HDPE), the microspheres were formed by evaporative removal of the acetone with an outlet temperature of the process chamber 160 of about 45° C. A 56% yield (3.09 g) of microspheres was collected as a free-flowing powder using a cyclone separator.

Example 5

In an embodiment of the microsphere manufacturing process described herein, 489 g of 4.5% poly lactide-co-glycolide (PLGA) 85:15 solution in acetone was prepared in feed vessel 135. To this solution was added 0.396 g of 5-Fluorouridine (5-FUD). The resulting solution was transferred at a rate of about 55 g/min via fluid delivery system 145 into the reservoir 708 of a spinning disk 105 having a diameter of about 76.2 mm, rotating at a rate of about 5,500 rpm. Utilizing a process chamber 160 comprising an internal surface of high-density polyethylene (HDPE), the microspheres were formed by evaporative removal of the acetone with an outlet temperature of the process chamber 160 of about 45° C. A 70% yield (15.55 g) of microspheres was collected as a free-flowing powder using a cyclone separator.

Example 6

In an embodiment of the microsphere manufacturing process described herein, 100 g of 5% poly lactide-co-glycolide (PLGA) 75:25 solution in 90:10 acetone/ethyl acetate was prepared in feed vessel 135. To this solution was added 0.56 g of Isopropyl (Z)-7-[(1R,2R,3R,5S)-3,5-dihydroxy-2-[(1E, 3R)-[3-hydroxy-4-[($\alpha,\alpha,\alpha$-trifluoro-m-tolyl)oxy]]-1-butenyl]cyclopentyl]-5-heptenoate. The resulting solution was transferred at a rate of about 71 g/min. via fluid delivery system 145 into the reservoir 708 of a spinning disk 105 having a diameter of about 76.2 mm, rotating at a rate of about 5,500 rpm. Utilizing a process chamber 160 comprising an internal surface of high-density polyethylene (HDPE), the microspheres were formed by evaporative removal of the acetone with an outlet temperature of the process chamber 160 of about 46° C. A 68% yield (3.8 g) of microspheres was collected as a free-flowing powder using a cyclone separator.

Example 7

In an embodiment of the microcapsule manufacturing process described herein, 42.7 g of a triglyceride (Sterotex NF, available from Abitec Corp., Janesville, Wis.) was melted in feed vessel 135 at a temperature of about 90-95° C. To the molten material was added 15.0 g of anecortave acetate, and the resulting dispersion was transferred at a rate of about 50-60 g/min. via fluid delivery system 145 into the reservoir 708 of a spinning disk 105 having a diameter of about 76 mm, rotating at a rate of about 7,500-8,500 rpm. Spinning disk 105 was maintained at a temperature of about 90-100° C. Microspheres were formed by cooling of the hotmelt with an outlet temperature of the process chamber 160 of about 22-28° C. An 80% yield (46.5 g) of microspheres was collected as a free-flowing powder using a cyclone separator. An over-coat was applied to a portion of the so produced microspheres. This was accomplished by preparing 100 g of a 5% solution of poly lactide-co-glycolide (PLGA) 75:25 in 60:40 acetone/ethyl acetate in feed vessel 135 and then dispersing therein 20.0 g of the microspheres. The resulting dispersion was transferred at a rate of about 120 g/min via fluid delivery system 145 into the reservoir 708 of a spinning disk 105 having a diameter of about 76.2 mm, rotating at a rate of about 3000-4000 rpm. The microspheres were formed by evaporative removal of the solvent with an outlet temperature of the process chamber 160 of about 45-50° C. A 71% yield (17.9 g) of microcapsules was collected using a cyclone separator.

In the Examples recited above, the spinning disk 105 utilized included the substantially flat surface 711 substantially parallel to the disk rotational axis beneath annular surface 706 proximate outer peripheral edge 707, and the teeth 712 disposed on the outer peripheral edge 707. The inclusion of surface 711 having this geometry facilitates the production of disks that have lower surface variability and therefore exhibit decreased wobbling during rotation. A conventional disk fabricated had a substantial horizontal and vertical displacement, which resulted in measurable "wobble" during rotation, but could be "tuned" to provide narrow particle size distributions by optimizing parameters such as fluid flow rate, fluid viscosity, disk rotation speed, and other variables known to those skilled in the art. However, while conventional disk operation could be so optimized, these optimum processing conditions were extremely narrow and processing outside these conditions resulted in significantly broader particle size distributions. In comparison, fabricating a conventional disk including a substantially flat surface 711 reduced the vertical and horizontal displacement to about 5-10 µm and the disk exhibited remarkably reduced levels of vibration during operation. Studies conducted indicate that lower vibrational levels resulted in reduced particle size variability compared to the conventional "wobbling" disk over a broad range of operating conditions.

Further studies conducted indicate the same phenomenon occurs with disks having the design of spinning disk 105 disclosed herein. A spinning disk 105 prepared without inclusion of a substantially flat surface 711 and having a disk variability of about 38 µm generally exhibited tighter particle size distributions than a similar disk 105 fabricated with a substantially flat surface 711 and having a surface variation of about 7.6 µm. However, analogous to the performance observed for the conventional disk, the general variability over a variety of operating conditions was lower for the spinning disk 105 comprising the substantially flat surface 711 than for similar disk 105 fabricated without a substantially flat surface 711. Not to be bound by theory, it is believed that the absence of disk vibration allows for better controlled particle breakup to occur on the disk surface resulting in narrower particle size distributions.

It is known that particle formation at a disk periphery can be influenced by the presence of evenly spaced conical tips or cones. See, e.g., Babu, S. R., "Analysis of Drop Formation at Conical Tips," *J. Colloid Interface Sci.*, 116 [2], 350-372 (1987). The inclusion of serrations or teeth 712 in spinning disk 105 greatly narrows the particle size distribution. Studies conducted comparing the particle size distribution of microparticles produced using a spinning disk 105 comprising a substantially flat surface 711, with and without teeth 712, indicate that the particle size distribution for the former is considerably narrow than for the latter. While this result is not necessarily unexpected, what is surprising is the magnitude of the decrease in particle size variability achieved with the "serrated" spinning disk 105.

Figure 9:
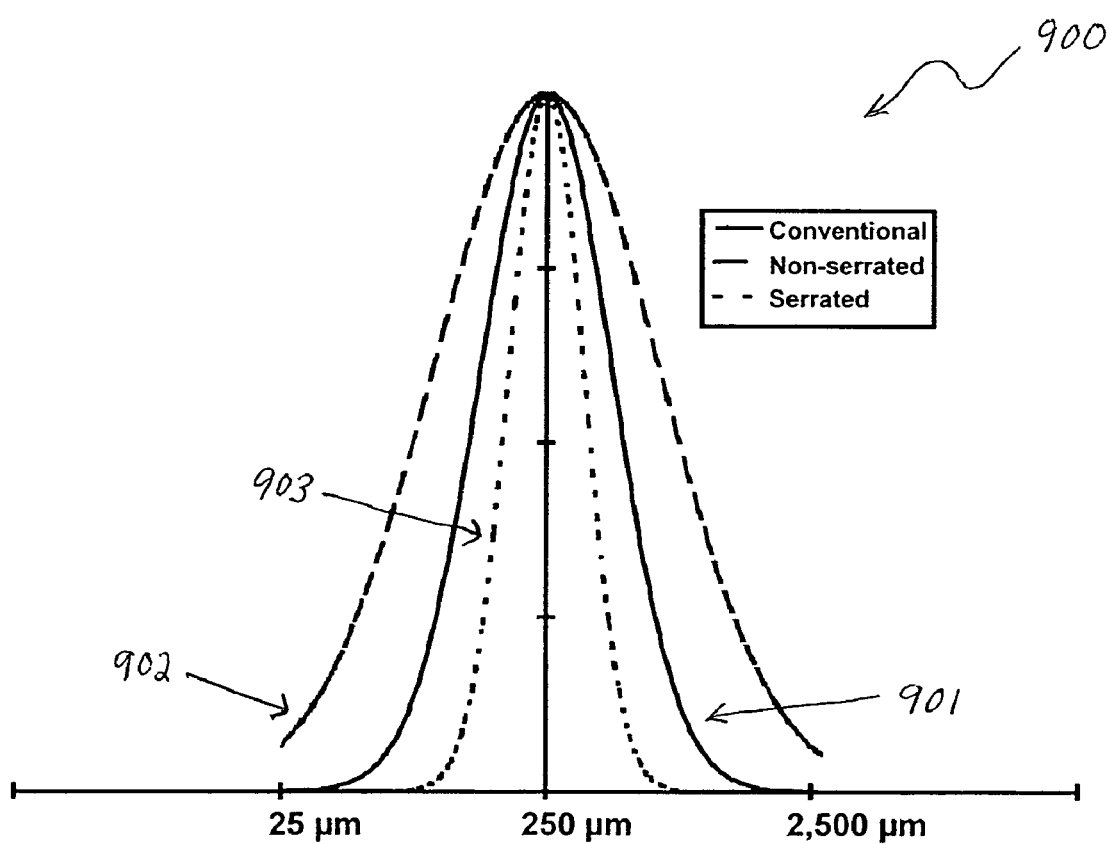
FIG. 9 shows particle size distribution curves generated by comparing a hypothetical population of microparticles produced with the spinning disk of the present invention and a conventional spinning disk.

For each of the non-serrated spinning disks tested that included a substantially flat surface 711 or the equivalent thereof, spinning disk 105 produced particle distributions that were on average 72% broader than particle populations produced by the conventional disk. The serrated spinning disk 105 produced the narrowest particle size distributions, which on average were 58% smaller than particle size distributions produced by the conventional disk. FIG. 9 graphically displays particle size distribution curves generated by comparing a hypothetical population of particles having an average diameter of 250 µm. As shown by graph 900 in FIG. 9, particles produced by the conventional disk would range in size from about 75 to 1000 µm (curve 901), particles produced by the non-serrated spinning disk 105 would range in size from about 25 to 2,500 µm (curve 902), and the particles from the serrated spinning disk 105 would range in size from about 175 to 500 µm (curve 903).

Disk wetting is another factor that influences microparticle formation, and therefore studies were conducted to determine the effects thereof on microparticle formation. While spinning disk 105 may be fabricated from any suitable material, the microparticle production examples disclosed herein were carried out using a stainless steel disk. A stainless steel disk surface is expected to have a high free energy, leading to limited wetting conditions. A conventional disk surface made of 304 stainless steel was initially conditioned by washing it with soapy water, then rinsing it with water followed by acetone, and finally drying the disk in air at 60° C. for one hour. The disk was then stored under nitrogen. Against this baseline, the disk surface was treated with a variety of materials, including Tergitol™ TMN-100 surfactant (available from Dow Corporation, Midland, Mich.), methanol, and water. Contact angle measurements were made upon application of various process solutions to the disk surface and observations were made while fluid was flowed across the disk surface during rotation of the spinning disk.

The studies indicate that repeatable microparticle formation is more readily achieved when the fluid flow across the disk surface achieves full wetting thereof. The results indicate that generally, the liquid surface tension of the process solution to be atomized on the spinning disk needs to be less than about 40 dynes/cm to ensure surface wetting of a clean, dry stainless steel disk. Alternatively, the disk surface free energy may be reduced by specific adsorption low free energy species or by fabricating the disk from intrinsically low free energy materials.

Figure 10:
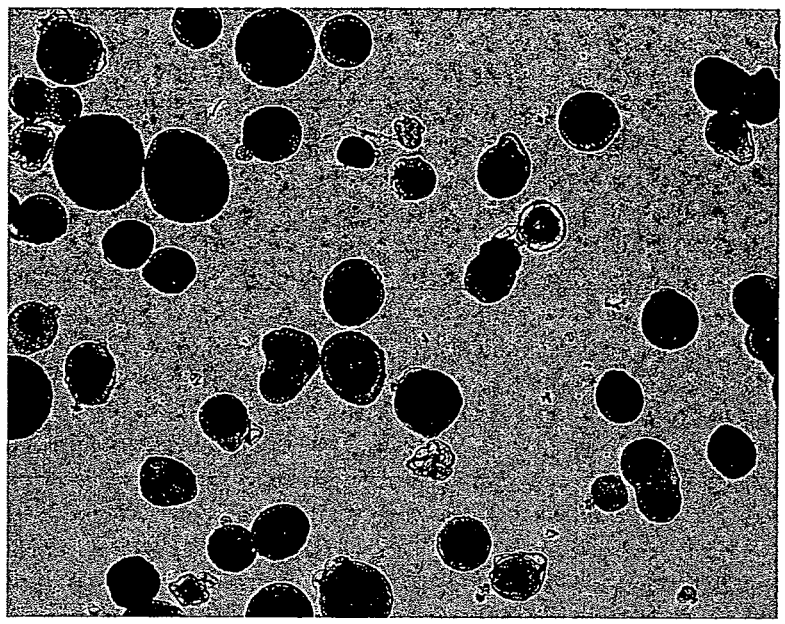
FIG. 10 shows a magnified image of microcapsules produced according to one embodiment of the present invention wherein a reduced number of placebo particles are formed.
Figure 11:
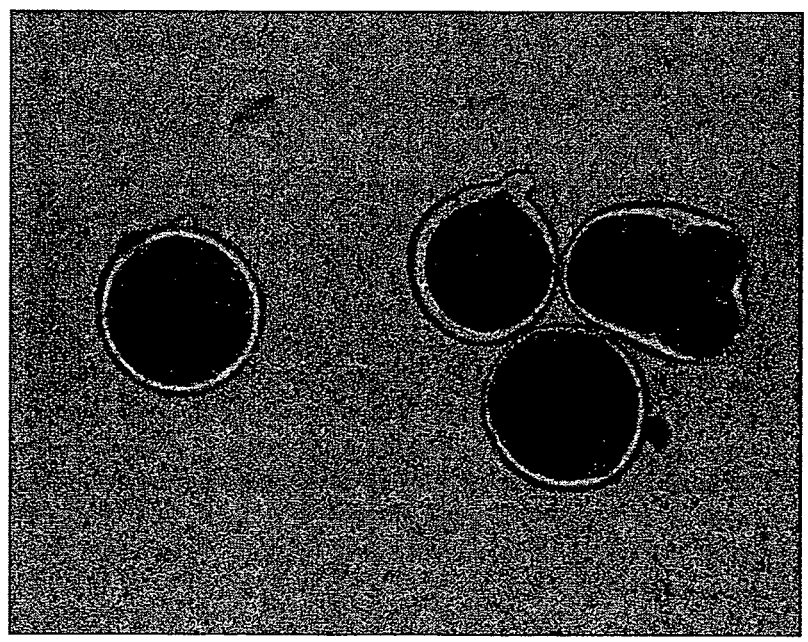
FIG. 11 shows a magnified image of microcapsules produced according to one embodiment of the present invention wherein the microcapsules manifest an improved coating uniformity.
Figure 12:
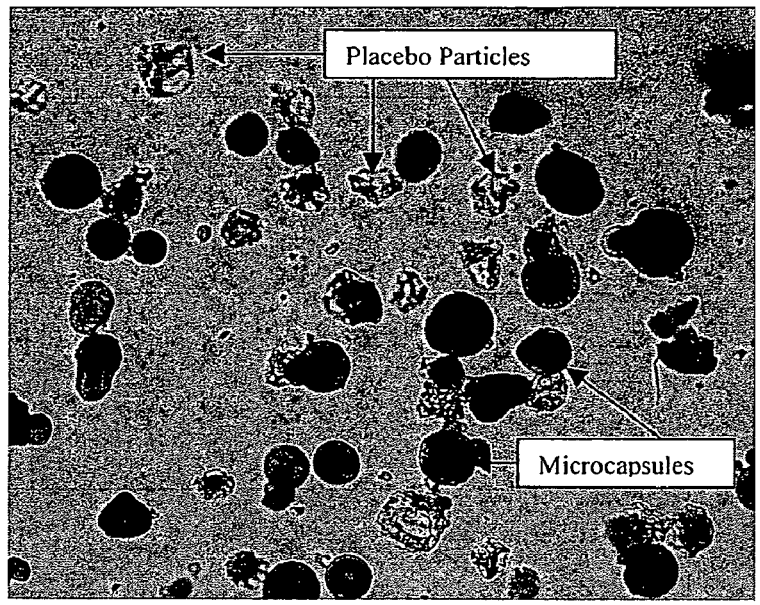
FIG. 12 shows a magnified image of microcapsules produced using a conventional spinning disk.
Figure 13:
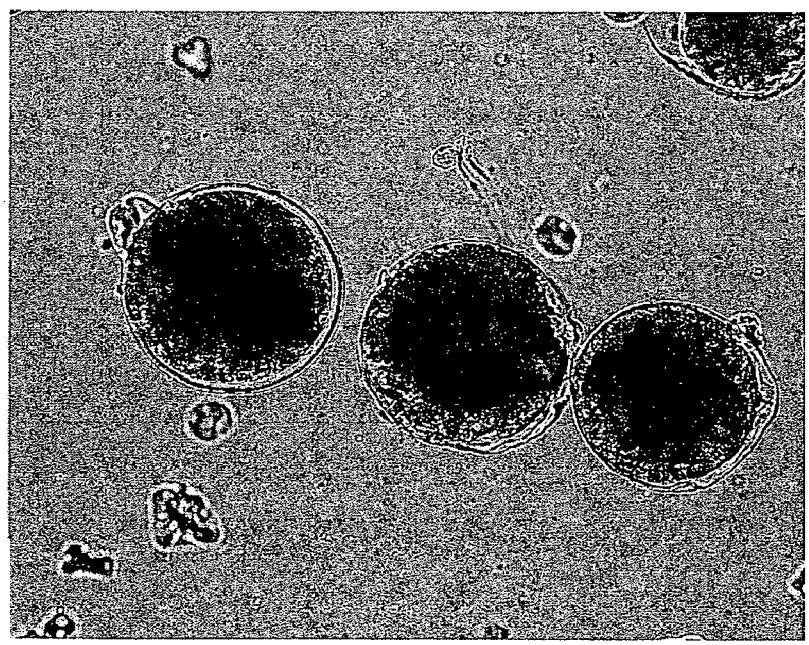
FIG. 13 shows another magnified image of microcapsules produced using a conventional spinning disk.

While reduced particle size variation is one objective of the present invention, another objective is the reduction of "pure" shell material particles (satellite or placebo particles) produced during microcapsule formation. One skilled in the art would know that by manipulating the viscosity of the polymer solution used in the overcoating process, one can reduce the amount of satellite particles produced. However, increasing polymer solution viscosity leads to, at some point, microsphere aggregation (overcoating of multiple microspheres to form one large microcapsule). By using the apparatus of the present invention to produce microcapsules, lower levels of placebo particles are typically formed and more uniform, thicker coatings can be applied. Microcapsule formation using a serrated spinning disk 105 comprising a substantially flat surface 711 can produce microcapsules containing significantly decreased levels of satellite particles (FIGS. 10 and 11) as compared to a process using a conventional disk (FIGS. 12 and 13). The reduction in placebo particles translates to an improved yield of microcapsules. In addition, as noted above, a more uniform, thicker coating can be applied using the apparatus of this invention compared to a conventional disk (FIG. 11 versus FIG. 13).

Another advantage of the present invention is reduced particle agglomeration. While as described above the design of spinning disk 105 allows for the production of microparticles having a narrow particle distribution, agglomeration of microparticles produced and collected causes problems in handling. The design features described above, such as thermally-controlled and/or low thermal conductivity surfaces, reduce particle agglomeration.

The apparatus of the present invention may be operated continuously as opposed to normal batch-wise manufacturing of microparticles. The following is given as an example of a 3-day continuous operation. About 400 kg of a 5% polycaprolactone solution in methylene chloride was prepared in feed vessel 135. To this solution was added 6.67 kg of anecortave acetate (25% payload), and the resulting dispersion was transferred at a rate of about 90 g/min via fluid delivery system 145 into the reservoir 708 of a spinning disk 105 having a diameter of about 76.2 mm, rotating at a rate of 3,000-4,000 rpm. The microspheres were formed by evaporative removal of the solvent with an outlet temperature of about 42-45° C. inside the plastic (HDPE) process chamber 160. A 93% yield (24.8 kg) of microspheres was collected as a free-flowing powder using a cyclone separator.

An additional advantage of the present invention is that microcapsules produced thereby exhibit improved active agent release properties. In an embodiment of the present invention, microspheres and microcapsules containing anecortave acetate as the active agent were prepared according to the methods described herein. The microparticles produced were sterilized by exposure to gamma radiation, at a dose level of 18-25 kGy. To measure the active agent release rates thereof, about 5.0 mg of the microparticles was weighed into glass bottles containing about 50 mL of a solution of 5% sodium dodecyl sulfate/phosphate (SDS/PBS) buffer solution. The sample bottles were then placed in a 37° C. shaking water bath. At various time intervals, 100 µL aliquots were removed for analysis and an equal volume of 5% SDS/PBS solution was replaced.

Figure 14:
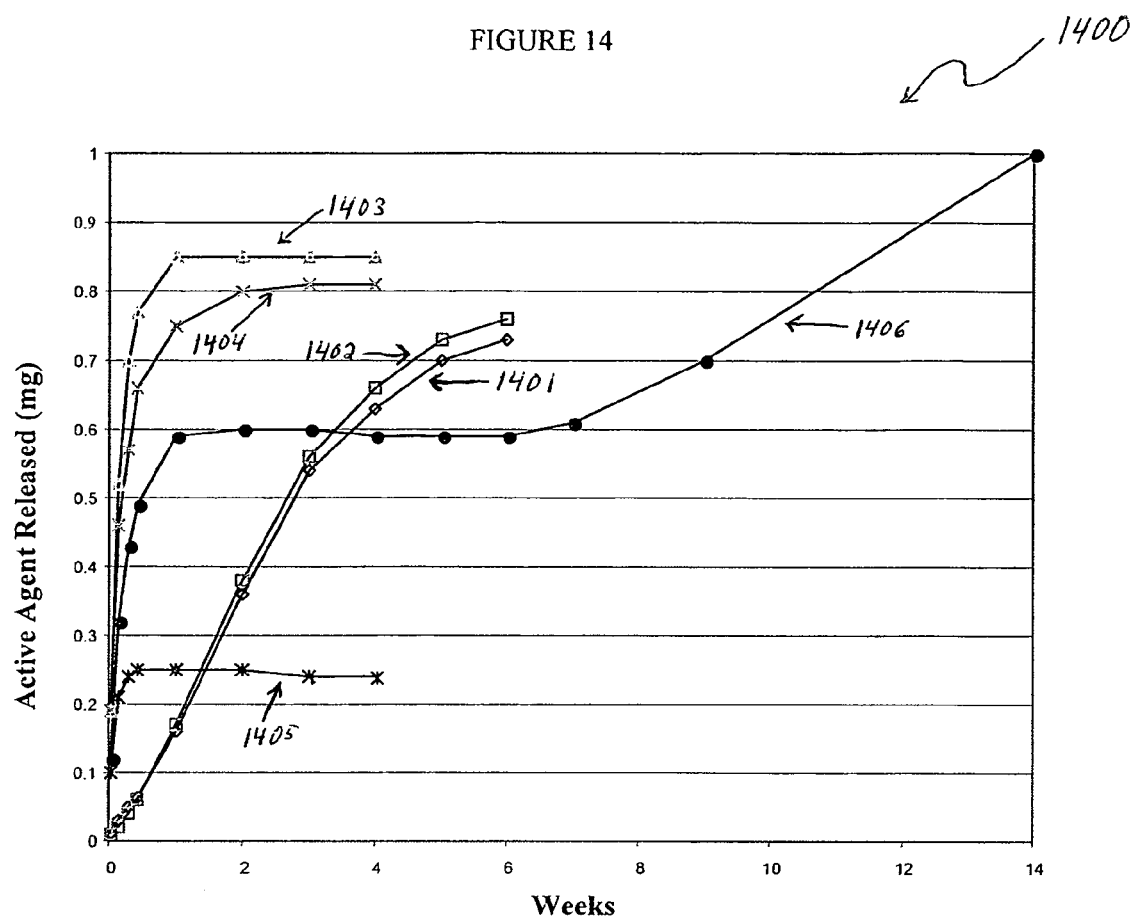
FIG. 14 shows a graph depicting the amount of the active agent released over time from various microparticles produced by the present invention.

As shown graphically in FIG. 14, a high payload (>20 wt. % active agent) microcapsule formulation provides a near zero-order release and a reduced burst release compared to the microsphere formulations. In FIG. 14, graph 1400 shows the amount of the active agent, anecortave acetate, released from various microparticles produced by the present invention and maintained in 5% SDS/PBS at 37° C. Curve 1401 shows the release profile of microcapsules (PLGA 75:25 coating covering microspheres comprising glyceride matrix) containing 23.8 wt. % active agent. Curve 1402 shows the release profile of microcapsules (PLGA 75:25 coating covering microspheres comprising glyceride matrix) containing 23.5 wt. % active agent. Curve 1403 shows the release profile of microspheres comprising PLGA 75:25/PEG (95:5) and containing 23.8 wt. % active agent. Curve 1404 shows the release profile of microspheres comprising PLGA 75:25/PEG (95:5) and containing 25.7 wt. % active agent. Curve 1405 shows the release profile of microspheres comprising PLGA 50:50/PEG (95:5) and containing 25.8 wt. % active agent. Curve 1406 shows the release profile of unsterilized microspheres comprising PLGA 50:50/PEG (95:5) and containing 24.6 wt. % active agent. Microcapsules and micrsopheres containing low payloads may exhibit zero order release, however at payloads above about 15%, especially where the encapsulated agent is highly soluble in the release medium, microspheres and microcapsules typically release most of the active agent very quickly (<1 day). The microcapsules of this invention with >20% active agent load do not show a rapid initial release in vitro, but rather a slow zero order release out to 4 weeks. (See curves 1401 & 1402 in FIG. 14). Control of the release rate is a very important component of the formulation where a rapid initial release could waste the active agent, or worse, be toxic to the recipient.

All patents and publications referenced herein, to the extent not previously herein incorporated by reference, are hereby incorporated by reference in their entirety to the extent not inconsistent with the disclosures in this Application. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

It is therefore, contemplated that the claims will cover any such modifications or embodiments that fall within the true scope of the invention.

What is claimed is:

1. A method for producing microparticles comprising:
   (A) introducing a composition to a spinning disk apparatus, wherein the composition comprises an active agent, and
   (B) operating the spinning disk apparatus to produce microparticles comprising the active agent, wherein, the spinning disk apparatus comprises a substantially circular spinning disk comprising:
      (i) a substantially smooth annular disk surface, wherein,
         (a) the annular disk surface has an inner peripheral edge and an outer peripheral edge, wherein the outer peripheral edge defines a first diameter of the annular disk surface,
         (b) the annular disk surface has a second diameter defined by the area circumscribed by the inner peripheral edge, wherein the area circumscribed by the inner peripheral edge is disposed substantially in a center portion of the spinning disk, and
         (c) the annular disk surface between the inner peripheral edge and the outer peripheral edge comprises a substantially flat incline; and
      (ii) a reservoir disposed in the area circumscribed by the inner peripheral edge of the annular disk surface, wherein
         (a) the reservoir comprises a top portion thereof defined by the inner peripheral edge of the annular disk surface, and
         (b) the reservoir is partially defined by a third diameter, located between the bottom of the reservoir and the top portion of the reservoir, wherein the third diameter is greater than the second diameter, and wherein, said introducing the composition to the spinning disk apparatus comprises introducing the composition to the reservoir; and
      (iii) a substantially flat surface beneath the annular disk surface proximate the outer peripheral edge, wherein the substantially flat surface lies in a plane that is substantially parallel to a rotational axis of the spinning disk, and wherein the substantially flat surface is between two surfaces, with each of said two surfaces lying in a plane different than the substantially flat surface.

2. The method of claim 1, wherein the microparticles consist essentially of microspheres and wherein said method further comprises:
   (A) combining the active agent with a matrix material to form the composition; and
   (B) operating the spinning disk apparatus to produce microspheres comprising the active agent and the matrix material.

3. The method of claim 1, wherein the microparticles consist essentially of microcapsules and wherein said method further comprises:
(A) combining a material comprising microspheres having the active agent with a coating material to form the composition; and
(B) operating the spinning disk apparatus to produce microcapsules comprising the microspheres having a coating comprising the coating material.

4. The method of claim 1, wherein the first diameter of the annular disk surface is between about 10 mm and about 300 mm.

5. The method of claim 1, wherein the first diameter of the annular disk surface and the second diameter of the annular disk surface are in a ratio between about 300:1 and about 2:1.

6. The method of claim 1, wherein the third diameter of the reservoir and the second diameter of the annular disk surface are in a ratio between about 20:1 and about 1.05:1.

7. The method of claim 1, wherein the substantially flat incline comprises an angle between about 5 degrees and about 45 degrees.

8. The method of claim 7, wherein the substantially flat incline comprises an angle between about 15 degrees and about 30 degrees.

9. The method of claim 1, wherein the outer peripheral edge of the annular disk surface comprises serrations.

10. The method of claim 9, wherein the serrations have a length between about 0 μm and about 5,000 μm.

11. The method of claim 10, wherein the serrations have a length between about 500 μm and about 1,500 μm.

12. The method of claim 9, wherein the serrations define an angle therebetween between about 105 degrees and about 15 degrees.

13. The method of claim 12, wherein the serrations define an angle therebetween between about 65 degrees and about 20 degrees.

14. The method of claim 1, wherein the substantially flat surface has a length between about 1 mm and about 10 mm.

15. The method of claim 1, wherein the spinning disk apparatus comprises a process chamber, wherein the process chamber comprises a material selected from the group consisting of a thermally controllable material, a low thermal conductivity material, and combinations thereof.

16. The method of claim 15, wherein the thermally controllable material comprises jacketed stainless steel.

17. The method of claim 15, wherein the low thermal conductivity material comprises plastic.

18. The method of claim 15, wherein the process chamber comprises a cone bottom tank, wherein the cone bottom tank comprises a material selected from the group consisting of a thermally controllable material, a low thermal conductivity material, and combinations thereof.

19. The method of claim 18, wherein the thermally controllable material comprises jacketed stainless steel.

20. The method of claim 18, wherein the low thermal conductivity material comprises plastic.

21. The method of claim 1, wherein the spinning disk apparatus comprises a sample collection system comprising a cyclone separator, wherein the cyclone separator comprises a material selected from the group consisting of a thermally controllable material, a low thermal conductivity material, and combinations thereof.

22. The method of claim 21, wherein the thermally controllable material comprises jacketed stainless steel.

23. The method of claim 21, wherein the low thermal conductivity material comprises plastic.

24. The method of claim 1, wherein the third diameter of the reservoir is disposed closer to the bottom of the reservoir than the top portion of the reservoir.

25. A method for producing microspheres comprising:
(A) combining an active agent with a matrix material to form a composition comprising the active agent and the matrix material,
(B) introducing the composition to a spinning disk apparatus, wherein the spinning disk apparatus comprises a substantially circular spinning disk comprising:
  (i) a substantially smooth annular disk surface, wherein
    (a) the annular disk surface has an inner peripheral edge and an outer peripheral edge, wherein the outer peripheral edge defines a first diameter of the annular disk surface,
    (b) the annular disk surface has a second diameter defined by the area circumscribed by the inner peripheral edge, wherein the area circumscribed by the inner peripheral edge is disposed substantially in a center portion of the spinning disk, and
    (c) the annular disk surface between the inner peripheral edge and the outer peripheral edge comprises a substantially flat incline; and
  (ii) a reservoir disposed in the area circumscribed by the inner peripheral edge of the annular disk surface, wherein
    (a) the reservoir comprises a top portion thereof defined by the inner peripheral edge of the annular disk surface, and
    (b) the reservoir is partially defined by a third diameter, located between the bottom of the reservoir and the top portion of the reservoir, wherein the third diameter is greater than the second diameter, wherein said introducing the composition to the apparatus comprises introducing the composition to the reservoir; and
  (iii) a substantially flat surface beneath the annular disk surface proximate the outer peripheral edge, wherein the substantially flat surface lies in a plane that is substantially parallel to a rotational axis of the spinning disk, and wherein the substantially flat surface is between two surfaces, with each of said two surfaces lying in a plane different than the substantially flat surface; and
(C) operating the apparatus to produce microspheres comprising the active agent and the matrix material.

26. The method of claim 25, wherein the matrix material comprises a biodegradable polymer.

27. The method of claim 26, wherein the biodegradable polymer comprises a material selected from the group consisting of poly lactic acids, poly glycolic acids, poly lactic-glycolic acids, polycaprolactone, triglycerides, poly ethylene glycols, poly orthoesters, polyanhydrides, polyesters, cellulosics, and combinations thereof.

28. The method of claim 25, wherein the active agent comprises a pharmacologically active agent.

29. The method of claim 28, wherein the pharmacologically active agent comprises a material selected from the group consisting of:
angiogenic inhibitors;
anti-inflammatory agents;
tyrosine kinase inhibitors;
anti-infectives;
anti-allergic agents;
cyclooxygenase inhibitors;
decongestants;
anti-glaucoma agents;

phosphatidyl-inositol kinase inhibitors;
gamma-aminobutyric acid and derivatives thereof;
antioxidants;
nutritional supplements;
agents for the treatment of cystoid macular edema;
agents for the treatment of age related macular degeneration;
agents for the treatment of herpetic infections;
agents for the treatment of cytomegalovirus ocular infections;
agents for the treatment of proliferative vitreoretinopathy;
wound modulating agents; anti-metabolites; neuroprotective drugs; angiostatic steroids; and combinations thereof.

30. The method of claim 25, wherein the active agent comprises an ophthalmically active agent.

31. The method of claim 30, wherein the ophthalmically active agent comprises a material selected from the group consisting of anecortave acetate, an alcohol form of anecortave acetate, derivatives thereof, and combinations thereof.

32. The method of claim 25, wherein the composition comprising the active agent and the matrix material is in a form selected from the group consisting of a solution, suspension, dispersion, molten mixture, and partially molten mixture.

33. The method of claim 25, wherein the composition comprising the active agent and the matrix material comprises a solvent.

34. The method of claim 33, wherein the solvent comprises a constituent compound selected from the group consisting of methanol, ethanol, methylene chloride, chloroform, ethyl acetate, and acetone.

35. The method of claim 25, wherein the microspheres produced have diameters substantially between about 1 μm and about 2,500 μm.

36. The method of claim 35, wherein the microspheres produced have diameters substantially between about 25 μm and about 300 μm.

37. The method of claim 25, wherein the microspheres produced have an active agent content substantially between about 0.001 wt. % and about 55 wt. %.

38. The method of claim 37, wherein the microspheres produced have an active agent content substantially between about 0.01 wt. % and about 30 wt. %.

39. A method for producing microcapsules comprising:
(A) combining a material comprising microspheres having an active agent with a coating material to form a composition comprising the microspheres and the coating material,
(B) introducing the composition to a spinning disk apparatus, wherein the spinning disk apparatus comprises a substantially circular spinning disk comprising:
(i) a substantially smooth annular disk surface, wherein
(a) the annular disk surface has an inner peripheral edge and an outer peripheral edge, wherein the outer peripheral edge defines a first diameter of the annular disk surface,
(b) the annular disk surface has a second diameter defined by the area circumscribed by the inner peripheral edge, wherein the area circumscribed by the inner peripheral edge is disposed substantially in a center portion of the spinning disk, and
(c) the annular disk surface between the inner peripheral edge and the outer peripheral edge comprises a substantially flat incline; and
(ii) a reservoir disposed in the area circumscribed by the inner peripheral edge of the annular disk surface, wherein
(a) the reservoir comprises a top portion thereof defined by the inner peripheral edge of the annular disk surface, and
(b) the reservoir is partially defined by a third diameter, located between the bottom of the reservoir and the top portion of the reservoir, wherein the third diameter is greater than the second diameter, wherein said introducing the composition to the apparatus comprises introducing the composition to the reservoir; and
(iii) a substantially flat surface beneath the annular disk surface proximate the outer peripheral edge, wherein the substantially flat surface lies in a plane that is substantially parallel to a rotational axis of the spinning disk, and wherein the substantially flat surface is between two surfaces, with each of said two surfaces lying in a plane different than the substantially flat surface; and
(C) operating the apparatus to produce microcapsules comprising the microspheres having a coating comprising the coating material.

40. The method of claim 39, wherein the coating material comprises a biodegradable polymer.

41. The method of claim 40, wherein the biodegradable polymer comprises a material selected from the group consisting of poly lactic acids, poly glycolic acids, poly lactic-glycolic acids, polycaprolactone, triglycerides, poly ethylene glycols, poly orthoesters, polyanhydrides, polyesters, cellulosics, and combinations thereof.

42. The method of claim 39, wherein the active agent comprises a pharmacologically active agent.

43. The method of claim 42, wherein the pharmacologically active agent comprises a material selected from the group consisting of:
angiogenic inhibitors;
anti-inflammatory agents;
tyrosine kinase inhibitors;
anti-infectives; anti-allergic agents;
cyclooxygenase inhibitors;
decongestants; anti-glaucoma agents;
phosphatidyl-inositol kinase inhibitors;
gamma-aminobutyric acid and derivatives thereof;
antioxidants;
nutritional supplements;
agents for the treatment of cystoid macular edema;
agents for the treatment of age related macular degeneration;
agents for the treatment of herpetic infections;
agents for the treatment of cytomegalovirus ocular infections;
agents for the treatment of proliferative vitreoretinopathy;
wound modulating agents;
anti-metabolites;
neuroprotective drugs;
angiostatic steroids; and
combinations thereof.

44. The method of claim 39, wherein the active agent comprises an ophthalmically active agent.

45. The method of claim 44, wherein the ophthalmically active agent comprises a material selected from the group consisting of anecortave acetate, an alcohol form of anecortave acetate, derivatives thereof, and combinations thereof.

46. The method of claim 39, wherein the composition comprising the microspheres and the coating material is in a form selected from the group consisting of a solution, suspension, dispersion, molten mixture, and partially molten mixture.

47. The method of claim 39, wherein the composition comprising the microspheres and the coating material comprises a solvent.

48. The method of claim 47, wherein the solvent comprises a constituent compound selected from the group consisting of methanol, ethanol, methylene chloride, chloroform, ethyl acetate, and acetone.

49. The method of claim 47, wherein the microspheres and active agent contained therein are not substantially soluble in the solvent.

50. The method of claim 39, wherein the microcapsules produced have diameters substantially between about 1 μm and about 2,500 μm.

51. The method of claim 50, wherein the microcapsules produced have diameters substantially between about 30 μm and about 300 μm.

52. The method of claim 39, wherein the microcapsules produced have a coating comprising between about 0.003 vol. % and about 50 vol. %.

53. The method of claim 52, wherein the microcapsules produced have a coating comprising between about 0.004 vol. % and about 5 vol. %.

54. The method of claim 39, wherein the microcapsules produced have an active ingredient content substantially between about 0.001 wt. % and about 50 wt. %.

55. The method of claim 54, wherein the microcapsules produced have an active ingredient content substantially between about 0.01 wt. % and about 30 wt. %.

56. The method of claim 39, wherein the microspheres are made by the method of claim 26.

57. The method of claim 56, wherein the spinning disk apparatus utilized in the method to produce the microspheres is selected from the group consisting of:
 (A) the same spinning disk apparatus utilized to produce the microcapsules; and
 (B) a different spinning disk apparatus than utilized to produce the microcapsules.

* * * * *